(12) United States Patent
Sampas et al.

(10) Patent No.: US 8,036,835 B2
(45) Date of Patent: Oct. 11, 2011

(54) PROBE DESIGN METHODS AND MICROARRAYS FOR COMPARATIVE GENOMIC HYBRIDIZATION AND LOCATION ANALYSIS

(75) Inventors: Nicholas M. Sampas, San Francisco, CA (US); Bo Curry, Redwood City, CA (US); Peter Tsang, San Francisco, CA (US); Doron Lipson, Tel-Aviv (IL); Zohar H. Yakhini, Ramat Hasharon (IL)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 12/797,521

(22) Filed: Jun. 9, 2010

(65) Prior Publication Data

US 2010/0279883 A1    Nov. 4, 2010

Related U.S. Application Data

(62) Division of application No. 10/996,323, filed on Nov. 23, 2004, now abandoned.

(51) Int. Cl.
*G06F 7/00* (2006.01)
(52) U.S. Cl. ............... 702/19; 702/20; 703/11; 703/12; 707/700
(58) Field of Classification Search .................. None
See application file for complete search history.

(56) References Cited

U.S. PATENT DOCUMENTS

| | | | |
|---|---|---|---|
| 5,348,855 A | 9/1994 | Dattagupta et al. | |
| 5,447,841 A | 9/1995 | Gray et al. | |
| 5,665,549 A | 9/1997 | Pinkel et al. | |
| 5,830,645 A | 11/1998 | Pinkel et al. | |
| 5,948,902 A | 9/1999 | Honkanen et al. | |
| 5,965,362 A | 10/1999 | Pinkel et al. | |
| 6,159,685 A | 12/2000 | Pinkel et al. | |
| 6,171,797 B1 | 1/2001 | Perbost | |
| 6,180,351 B1 | 1/2001 | Cattell | |
| 6,197,501 B1 | 3/2001 | Cremer et al. | |
| 6,210,878 B1 | 4/2001 | Pinkel et al. | |
| 6,232,072 B1 | 5/2001 | Fisher | |
| 6,242,266 B1 | 6/2001 | Schleifer et al. | |
| 6,251,588 B1 | 6/2001 | Shannon et al. | |
| 6,251,601 B1 | 6/2001 | Bao et al. | |
| 6,323,043 B1 | 11/2001 | Caren et al. | |
| 6,335,167 B1 | 1/2002 | Pinkel et al. | |
| 6,465,182 B1 | 10/2002 | Gray et al. | |
| 2002/0006622 A1 | 1/2002 | Bradley et al. | |
| 2003/0099964 A1 | 5/2003 | Patil et al. | |

FOREIGN PATENT DOCUMENTS

| | | |
|---|---|---|
| WO | WO 93/18186 | 9/1993 |
| WO | WO 99/23256 | 5/1999 |
| WO | WO 01/05935 | 1/2001 |
| WO | WO 01/23600 | 4/2001 |

OTHER PUBLICATIONS

Angerer et al. In situ hybridization to cellular RNAs. Genetic Engineering: Principles and Methods, Setlow and Hollaender, Eds. 1981, vol. 7, pp. 43-65.
Brennan et al. High-resolution global profiling of genomic alterations with long oligonucleotide microarray. Cancer Research. 2004, vol. 64, pp. 4744-4748.
Breslauer et al. Predicting DNA duplex stability from the base sequence. PNAS. 1986, vol. 83, pp. 3746-3750.
Cai et al. Genome-wide detection of chromosomal imbalances in tumors using BAC microarrays. Nature Biotechnology. 2002, vol. 20, pp. 393-396.
Conlon et al. Integrating regulatory motif discovery and genome-wide expression analysis. PNAS. 2003, vol. 100, pp. 3339-3344.
Dong et al. Flexible use of high-density oligonucleotide arrays for single-nucleotide polymorphism discovery and validation. Genome Research. 2001, vol. 11, pp. 1418-1424.
Galla et al. Pyrenedecanoic acid and pyrene lecithin. Methods in Enzymology. 1981, vol. 72, pp. 470-480.
Hodgson et al. Genome scanning with array CGH delineates regional alterations in mouse islet carcinomas. Nature Genetics. 2001, vol. 29, pp. 459-464.
Kallioniemi et al. Comparative genomic hybridization for molecular cytogenetic analysis of solid tumors. Science. 1992, vol. 258, pp. 818-821.
Lee et al. Human centromeric DNAs. Human Genetics. 1997, vol. 100, pp. 291-304.
Lee et al. Multi-objective evolutionary probe design based on thermodynamic criteria for HPV detection. PRICAI 2004, LNAI 3157. 2004, pp. 742-750.
Nielsen et al. Design of oligonucleotides for microarrays and perspectives for design of multi-transcriptome arrays. Nucleic Acids Research. 2003, vol. 31, pp. 3491-3496.
Pinkel et al. High resolution analysis of DNA copy number variation using comparative genomic hybridization to microarrays. Nature Genetics. 1998, vol. 20, pp. 207-211.
Pollack et al. Microarray reveals a major direct role of DNA copy number alteration in the transcriptional program of human breast tumors. PNAS. 2002, vol. 99, pp. 12963-12968.
Rabinovitch et al. Pancolonic chromosomal instability precedes dysplasia and cancer in ulcerative colitis. Cancer Research. 1999, vol. 59, pp. 5148-5153.
Snijders et al. Assembly of microarrays for genome-wide measurement of DNA copy number. Nature Genetics. 2001, vol. 29, pp. 263-264.

(Continued)

*Primary Examiner* — Mary Zeman
(74) *Attorney, Agent, or Firm* — James S. Keddie; Bret E. Field; Bozicevic, Field & Francis

(57) ABSTRACT

Methods and systems for identifying and selecting nucleic acid probes for detecting a target with a nucleic acid probe array or comparative genome hybridization microarray, comprising selecting a plurality of potential target sequences, generating a plurality of candidate probes from the target sequences, filtering the plurality of candidate probes by analyzing candidate probes for selected probe properties in silico. Microarrays comprising probes selected by the methods of the invention are particularly useful for comparative genome hybridization and location analysis.

20 Claims, 17 Drawing Sheets

OTHER PUBLICATIONS

Sugimoto et al. Improved thermodynamic parameters and helix initiation factor to predict stability of DNA duplexes. Nucleic Acids Research. 1996, vol. 24, pp. 4501-4505.

Talla et al. A novel design of whole-genome probes for Saccharomyces cerevisiae which minimizes cross-hybridization. BMC Genomics. 2003, vol. 4, pp. 1-18.

Trask et al. Human cytogenetics: 46 chromosomes, 46 years and counting. Nature Genetics. 2002, vol. 3, pp. 769-778.

Trinklein et al. Identification and functional analysis of human transcriptional promoters. Genome Research. 2003, vol. 13, pp. 308-312.

Wilhelm et al. Array-based comparative genomic hybridization for the differential diagnosis of renal cell cancer. Cancer Research. 2002, vol. 62, pp. 957-960.

PROBE DESIGN METHODS AND MICROARRAYS FOR COMPARATIVE GENOMIC HYBRIDIZATION AND LOCATION ANALYSIS

FIELD OF THE INVENTION

The invention relates to methods for designing and selecting probes for microarrays, and in particular comparative genome hybridization arrays and for location analysis.

BACKGROUND OF THE INVENTION

Comparative Genomic Hybridization (CGH) and location analysis are important applications, which allow scientists to improve their understanding of the expression and regulation of genes in biological systems. Both CGH and location analysis entail quantifying or measuring changes in copy number of genomic sequences. CGH, is particularly important in developmental biology as well as the causes of cancer and offers great potential in the diagnostics of cancer and developmental diseases. Recently, cDNA microarrays have been used for CGH studies. An oligo-array based approach has several substantial advantages over other technologies, in that it allows the designer to position the probes anywhere within the genomic or polynucleotide sequence of interest. The probes can be placed at whatever density is commensurate with the real-estate or area available on the microarray (in terms of number of features) and the genomic regions of interest can be evaluated by analyzing the hybridization of target sequences to the surface-bound probes. The oligonucleotide probe approach also offers the flexibility of focusing in on regions within exons or introns of expressed sequences, or intergenic regions and regulatory regions for location analysis, as well as any desirable admixture of the aforementioned.

Probes that work well on microarrays for gene expression generally do not work well for CGH arrays and are not appropriate for location analysis arrays. The overall performance of probes for CGH and location analysis arrays entails different optimization of their properties than probes utilized for gene expression. Most notably, these differences relate to the substantially increased complexity of the labeled target mixture for CGH and location analysis than for expression analysis which demands a greater specificity of the probes in discriminating against non-specific binding to competing targets. For comparison, the total number of nucleotide bases in the human transcriptome is approximately $10^8$, while the human genome contains over $3 \times 10^9$ bases. Additionally, probes selected for gene expression come from within message sequences that are transcribed as RNA, i.e. exons, while probes for CGH need be complementary, or nearly so, to contiguous targets selected from within a genome sequence e.g. introns and/or exons.

With increased target complexity comes increased flexibility in the choice of probes. For example, many methods for gene expression restrict probe design to several hundred bases of the 3'-end of the target (message) sequence. Thus, limiting the probe designer to a choice of one in about 500-1000 discrete positions where a probe can be started within any given gene (or transcript). However, for CGH probe design, scientists have a much broader region in which to chose a probe for any given gene. This region may include introns as well as exons and is typically hundreds of thousands of bases long, and in some cases even millions of bases in length.

For location analysis probe design, scientists have a specific region in which to identify and design probes. While the probe designer is constrained to selecting probes within regulatory regions, regions upstream of genes and/or specific locations of interest, the overall number of bases which must be screened is much larger and broader than the region analyzed for gene expression probe design.

Despite great interest in CGH technology, methods for evaluating probes in silico and also empirically for use in this technology are limited. A rigorous method would be to measure signals (e.g. ratios) from each polynucleotide in controlled experiments with test samples containing known copy numbers for each sequence on the array. For example, a method used by several probe designers for measuring array performance for sets of polynucleotides specific for sequences on the X chromosome, is to use a series of cell lines with known variable copies of the X chromosome for CGH experiments. These cell lines (X series) contain intact copies (e.g. 1 to 5) of the X chromosome permitting a rigorous measure of the relationship between copy number and signal intensities for each X chromosome specific polynucleotide on an array.

However, cell lines containing known variable numbers of intact copies of other chromosomes besides for the X chromosome in the genome are not readily available. Furthermore, the aberrant X series cell lines are slow growing and can spontaneously vary in ploidy under standard culturing conditions. Such methods are complex and time-consuming and cannot readily be used to assay the relationship between the hybridization signal of polynucleotides on an array and the genomic copy number of sequences from each chromosome in a cell.

Accordingly, a great need exists for methods for designing and evaluating surface-bound CGH probe nucleic acids (i.e. probes) as well as microarrays comprising these probes which have been identified to have probe properties which make them well suited for CGH and location analysis. This invention meets this, and other, needs.

Relevant Literature

United States patents of interest include: U.S. Pat. Nos. 6,465,182; 6,335,167; 6,251,601; 6,210,878; 6,197,501; 6,159,685; 5,965,362; 5,830,645; 5,665,549; 5,447,841 and 5,348,855. Also of interest are published United States Application Serial No. 2002/0006622 and published PCT application WO 99/23256. Articles of interest include: Pollack et al., Proc. Natl. Acad. Sci. (2002) 99: 12963-12968; Wilhelm et al., Cancer Res. (2002) 62: 957-960; Pinkel et al., Nat. Genet. (1998) 20: 207-211; Cai et al., Nat. Biotech. (2002) 20: 393-396; Snijders et al., Nat. Genet. (2001) 29:263-264; Hodgson et al., Nat. Genet. (2001) 29:459-464; Trask, Nat. Rev. Genet. (2002) 3: 769-778; Rabinovitch et al., Cancer Res. (1999) 59:5148-5153; Lee et al., Human Genet. (1997) 100:291:304; Conlon et al. PNAS (2003) 100:3339-3344; Trinklein et al. Genome Res. (2003) 308-312; J Breslauer et al. Proc Natl Acad Sci. (PNAS) 1986 June; 83(11): 3746-3750; Naoki Sugimoto et al. Nucleic Acids Research, V24, 4505, 1996.

SUMMARY OF THE INVENTION

Methods for designing and identifying probes for array based measurements of genomic copy number for comparative genomic hybridization and location analysis are provided. Specifically, a method for generating candidate probes from a target sequence or genomic sequence of interest, repeat-masking the target sequence to form non-repeat masked regions; and tiling, generating a periodic set of sequences across the non-repeat masked regions to generate the candidate probes.

The above method may further comprise screening the candidate probes according to at least one of several in silico parameters and or properties. The method of the invention may also comprise screening the candidate probes according to at least one experimentally measurable parameter or property. The method may further comprise validating the candidate probes by target hybridization experiments.

In some embodiments, the method may further comprise identifying restriction cut sites within the target sequence, and selecting target sequences that exclude or are bounded by these restriction sites when generating candidate probes. Filtering out target sequences with restriction cut sites, reduces the number of possible candidate probes prior to other components of in silico analysis and decreases the amount computational time needed to evaluate the candidate probes.

In other embodiments, the screening according to the in silico parameters comprises annotating the candidate probes for expression and association with the genes of interest. The screening may also comprise analyzing the candidate probes for target specificity and/or thermodynamically annotating the candidate probes. In yet another embodiment, the in silico parameters may comprise a parameter for kinetic properties of the candidate probes.

Methods which comprise in silico annotation may include annotating the candidate probes for their thermodynamic properties, such as duplex melting temperature and/or hairpin stability of the candidate probes. Where the methods of the invention comprise a parameter for duplex melting temperature, the duplex melting temperature may be estimated by the GC-content of the candidate probes. An accurate determination of the melting temperature of oligonucleotide hybridization is achieved by a use of a model that considers nearest-neighbor interactions as represented by the nearest-neighbor parameters.

In other embodiments of the invention, the in silico parameters may comprise a parameter for duplex stability for the candidate probes. In some methods, the duplex stability parameter evaluates the candidate probes for a property selected from the group consisting of melting temperature, entropy, enthalpy and Gibb's free energy. In other embodiments, the hairpin structural stability parameter for the probe, and the target stability parameters may be determined by evaluating the candidate probes for a property selected from the group consisting of melting temperature, entropy, enthalpy and Gibb's free energy. Alternatively, the in silico parameters may be target specificity, and/or target secondary structural stability, where target structural stability is evaluated by a property selected from the group consisting of melting temperature, entropy, enthalpy and Gibb's free energy.

In other methods of the invention, the in silico parameters may comprise a parameter that is the maximum subsequence melting temperature of the probe. This is the maximum duplex melting for any contiguous sub-sequence of a probe with its complementary target, where all possible subsequences of length L are considered and where L is less than the probe length. This metric has been found to be informative in filtering out probes that have GC-rich regions that appear to act as nucleation sites for non-specific hybridization. For the probes we designed, with nominal lengths of 60 bp, the lengths of L of interest spanned from 15-30 bp.

In other methods of the invention, the in silico parameters may comprise a parameter for intergenicity of the candidate probes. When the parameter for intergenicity is utilized, this parameter evaluates whether the candidate probe sequence is within a gene, in between a gene or within a coding region of a gene.

In other methods, the in silico parameters comprise a parameter for expression of the candidate probes. When the parameter for expression is utilized, this parameter evaluates whether the candidate probe sequence is within a gene, the candidate probe sequence is within an expression region of a gene, or the candidate probe sequence is within a coding region of a gene.

Additionally, the in silico parameters may include the specificity of the probe to it's intended target. The method of the invention may also comprise determining a homology score expressed as an effective signal-to-background for each candidate probe in silico. The homology signal-to background score for each candidate probe may be expressed in the form of HomLogS2B.

In other embodiments, the method comprises applying a pairwise probe selection process to the candidate probes. Applying pairwise selection comprises analyzing neighboring probe sequences within a genomic region of interest, evaluating the pair of neighboring probe sequences for a probe property and then scoring the neighboring probe sequences for the probe property, or properties, of interest. The pairwise filtering algorithm is a means of reducing the size of a set of candidate probes to a smaller set of probes, while enriching for a specific beneficial property or properties. In the methods where the pairwise analysis is utilized, the probe property may be selected from the group consisting of duplex melting temperature, hairpin stability, GC content, if the probe is within an exon, probe is within a gene, probe is within an intron and probe is within a intergenic region, or any property or score for combined properties of the probe or the gene in which it is contained.

In other embodiments, the method may comprise applying a biased pairwise probe filtering analysis to the candidate probes. Applying a biased pairwise selection algorithm comprises, analyzing neighboring probe sequences within a genomic region of interest, evaluating the neighboring probe sequences for a first probe property or group of properties, evaluating the neighboring probe sequences for a second probe property or group of properties and scoring the neighboring probe sequences for the first probe property and weighting this scoring process by the presence or absence of the second probe property. When biased pairwise analysis is utilized, the probe properties of the first and second parameters are selected from the group consisting of duplex melting temperature, hairpin stability, GC content, probe is within an exon, probe is within a gene, probe is within an intron and probe is within a intergenic region as well as any second property or score for combined properties of the probe or the gene in which it is contained. Alternatively, the pairwise filtering selection algorithm may utilize a single score which combines multiple properties into a single value for each probe.

Alternatively, applying pairwise selection analysis may comprise selecting a plurality of probe pairs, each probe pair comprising a first probe sequence and a second probe sequence which are adjacent probe sequences within the chromosome of interest, evaluating the first and second probe sequences for at least one probe property, assigning at least one score for each probe property to the first and second probe sequences, and determining which probe sequence of each probe pair comprises the optimum probe characteristics for said microarray. In some embodiments the probe pairs are randomly selected for pairwise analysis while in other embodiments the probe pairs are selected for pairwise analysis by the order in which they target the chromosome or gene sequence of interest. The order may be assigned in the 3' to 5' direction or 5' to 3' direction. In a preferred embodiment that leads to the construction of more uniformly spaced probe sets, the probe pairs are ordered by the base pair gap size between the first and second probe sequences. Either ordering the pairs by smallest gap distance to largest or largest gap to smallest gap distance. The probe properties selected for pairwise analysis may be selected from the group consisting of duplex melting temperature, hairpin stability, GC content, if probe is within an exon, probe is within a gene, probe is within an intron and probe is within an intergenic region.

In certain embodiments the methods of the invention when candidate probes are screened according to at least one experimentally measurable parameter or property, the experimentally measurable property or parameter is selected from the group consisting of signal intensity, reproducibility of signal intensity, dye bias, susceptibility to non-specific binding, wash stability and persistence of probe hybridization. In embodiments where experimentally validating candidate probe performance is used for probe selection, validating the candidate probes comprises hybridizing the candidate probes to a plurality of target sets, evaluating the candidate probes for a probe property for each target set, and comparing the values for probe property of each candidate probe across a plurality of target sets.

In most embodiments of the methods of the invention, computer readable medium carrying one or more sequences of instructions for identifying and selecting nucleic acid probes for detecting a target with a probe array is needed. Where the execution of one or more sequences of instructions by one or more processors causes the one or more processors to perform the steps of, repeat-masking said target sequences to form non-repeat masked regions; and tiling sequences across said non-repeat masked regions to generate said candidate probes. In certain embodiments, the steps performed by one or more processors further comprises identifying restriction cut sites in a chromosome of interest, and selecting target sequences that exclude the restriction sites.

The microarrays of the invention comprise a solid support a plurality of polynucleotide probes attached to the support, the plurality of polynucleotide probes having a corresponding plurality of different nucleotide sequences, and at least 50% of the polynucleotide probes have a duplex $T_m$ within a temperature range of about 75° C. to about 85° C. In most embodiments that microarrays of the invention have at least 1,000 polynucleotide probes surface bound to the support, more likely at least 2,000 polynucleotide probes, and usually at least 10,000 polynucleotide probes. In most embodiments at least 20,000 polynucleotide probes are surface bound, and usually at least 40,000 polynucleotide probes are bound to the solid support. In some embodiments, over 100,000 probes are bound to the solid support and in some embodiments the number of probes on the microarray is larger than 400,000.

In one embodiment, at least 80% of said polynucleotide probes have a duplex $T_m$ within a temperature range of about 75° C. to about 85° C., usually about 77° C. to about 83° C., more usually from about 78° C. to about 82° C. and even more usually about 79° C. to about 82° C. Alternatively, the microarray will have at least 90% of said polynucleotide probes have a duplex $T_m$ within said temperature range of about 75° C. to about 85° C., usually about 77° C. to about 83° C., more usually from about 78° C. to about 82° C. and even more usually about 79° C. to about 82° C. The determination of $T_m$ values for probes is dependent on many factors and may vary widely depending on the method or calculation utilized for calculating $T_m$s. Thus it is useful to describe the invention in terms of a delta $T_m$ value or range in which a large portion of the polynucleotide probes have a $T_m$ value which fall within this delta $T_m$.

In other embodiments, the microarray comprises a solid support and a plurality of polynucleotide probes attached to the support, the plurality of polynucleotide probes having a corresponding plurality of different nucleotide sequences, and at least 50% of the polynucleotide probes have a duplex Tm within a delta Tm of less than 4° C., usually less then 3° C., more usually 2° C. Alternatively, at least 50% of the polynucleotide probes have a duplex Tm within a delta Tm of less than 1.5° C., usually less than 1.0° C., and more usually 0.5° C.

In other embodiments, at least 80% of the polynucleotide probes have a duplex Tm within a delta Tm of less than 4° C., usually less then 3° C., more usually 2° C. Alternatively, at least 80% of the polynucleotide probes have a duplex Tm within a delta Tm of less than 1.5° C. In yet other embodiments, at least 90% of the polynucleotide probes have a duplex Tm within a delta Tm of less than 4° C., usually less then 3° C., more usually 2° C.

The probes on the microarray, in certain embodiments have a nucleotide length in the range of at least 30 nucleotides to 100 nucleotides. In other embodiments, at least 50% of the polynucleotide probes on the solid support have the same nucleotide length, and that length may be about 60 nucleotides.

In some embodiments, at least 5% of the polynucleotide probes on the solid support hybridize to regulatory regions of a nucleotide sample of interest while other embodiments may have at least 30% of the polynucleotide probes on the solid support hybridize to exonic regions of a nucleotide sample of interest. In yet other embodiments, at least 50% of the polynucleotide probes on the solid support hybridize intergenic regions of a nucleotide sample of interest.

In certain embodiments the polynucleotide probes are structured and configured for analysis of a nucleotide sample by comparative genome hybridization and/or location analysis. The microarrays wherein The nucleotide sequences of the polynucleotide probes hybridize to nucleotide samples generated the human genome in some embodiments while other microarrays comprise polynucleotide probes with nucleotide sequences which hybridize to nucleotide samples from the mouse genome.

In other embodiments, a microarray comprises a solid support; and a plurality of polynucleotide probes attached to the support, the plurality of polynucleotide probes having a corresponding plurality of different nucleotide sequences, where about 60% to about 90% of the polynucleotide probes have a percent GC content within a delta percent GC of 10%. Alternatively about 70% to about 90% of said polynucleotide probes have a percent GC content within a delta percent GC of 10%, and usually about 80% to about 90% of said polynucleotide probes have a percent GC content within a delta percent GC of 10%. In other embodiments, about 40% to about 90% of said polynucleotide probes have a percent GC content within a delta percent GC of 5% and usually about 60% to about 90% of said polynucleotide probes have a percent GC content within a delta percent GC of 5% and more usually about 70% to about 90% of said polynucleotide probes have a percent GC content within a delta percent GC of 5%.

In other embodiments, about 35% to about 80% of the polynucleotide probes have a percent GC content within a delta percent GC of 3%, usually about 40% to about 70% of said polynucleotide probes have a percent GC content within a delta percent GC of 3% and more usually about 40% to about 65% of said polynucleotide probes have a percent GC content within a delta percent GC of 3%.

In yet other embodiments, at least 70%, usually at least 75%, more usually at least 80%, and even more usually at least 85% of the polynucleotide probes have a percent GC content within a delta percent GC of 10%. In other embodiments, at least 60%, and usually at least 70%, of the polynucleotide probes have a percent GC content within a delta percent GC of 5%. In another embodiment, at least 40%, and usually at least 50%, and more usually at least 60% of the polynucleotide probes have a percent GC content within a delta percent GC of 3%.

The present invention also provides a computer readable medium carrying one or more sequences of instructions for identifying and selecting nucleic acid probes for detecting a target with a probe array, wherein execution of one or more sequences of instructions by one or more processors causes the one or more processors to perform the steps of, identifying restriction cut sites in a chromosome of interest, selecting target sequences that exclude said restriction sites, repeat-masking the target sequences to form non-repeat masked regions, and tiling sequences across the non-repeat masked regions to generate the candidate probes.

These and other advantages and features of the invention will become apparent to those persons skilled in the art upon reading the details of the methods for probe selection and microarray composition useful for CGH and location analysis as more fully described below.

DETAILED DESCRIPTION OF THE INVENTION

Figure 1:
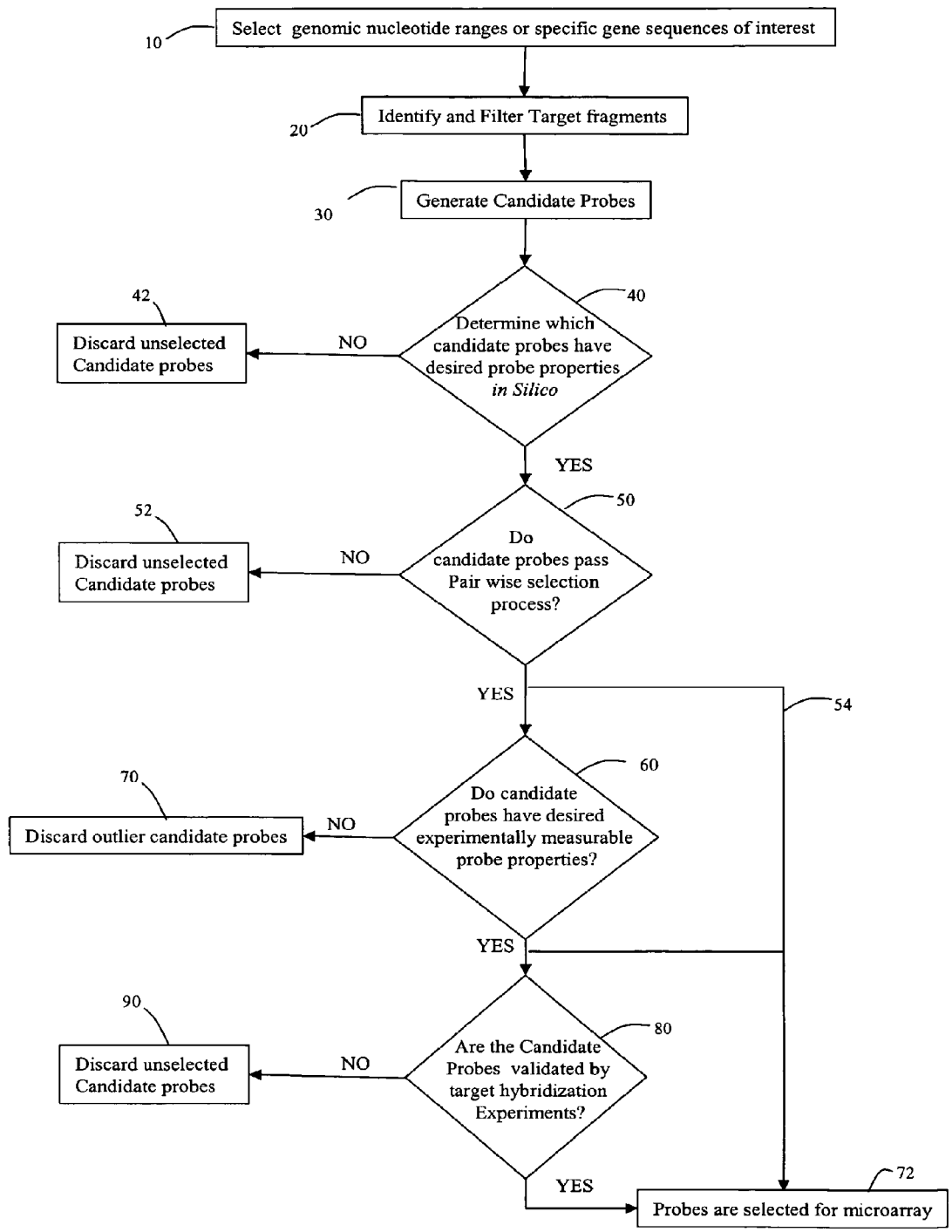
FIG. 1 is a flow chart of a process of probe selection utilizing probe selection parameters for CGH in accordance with the invention.

Before the present methods for CGH probe selection are described, it is to be understood that this invention is not limited to particular genes or chromosomes described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polynucleotide" includes a plurality of such polynucleotides and reference to "the target fragment" includes reference to one or more target fragment and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "nucleic acid" and "polynucleotide" are used interchangeably herein to describe a polymer of any length, e.g., greater than about 10 bases, greater than about 100 bases, greater than about 500 bases, greater than 1000 bases, usually up to about 10,000 or more bases composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length. Oligonucleotides are usually synthetic and, in many embodiments, are under 50 nucleotides in length.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other nucleic acids that are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "surface-bound polynucleotide" refers to a polynucleotide that is immobilized on a surface of a solid substrate, where the substrate can have a variety of configurations, e.g., a sheet, bead, or other structure. In certain embodiments, the collections of oligonucleotide probe elements employed herein are present on a surface of the same planar support, e.g., in the form of an array.

The phrase "labeled population of nucleic acids" refers to mixture of nucleic acids that are detectably labeled, e.g., fluorescently labeled, such that the presence of the nucleic acids can be detected by assessing the presence of the label. A labeled population of nucleic acids is "made from" a chromosome sample, the chromosome sample is usually employed as template for making the population of nucleic acids.

The term "array" encompasses the term "microarray" and refers to an ordered array presented for binding to nucleic acids and the like.

An "array," includes any two-dimensional or substantially two-dimensional (as well as a three-dimensional) arrangement of spatially addressable regions bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulsejets of either nucleic acid precursor units (such as monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180, 351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

An array is "addressable" when it has multiple regions of different moieties (e.g., different oligonucleotide sequences) such that a region (i.e., a "feature" or "spot" of the array) at a particular predetermined location (i.e., an "address") on the array will detect a particular sequence. Array features are typically, but need not be, separated by intervening spaces. In the case of an array in the context of the present application, the "population of labeled nucleic acids" will be referenced as a moiety in a mobile phase (typically fluid), to be detected by "surface-bound polynucleotides" which are bound to the substrate at the various regions. These phrases are synonymous with the arbitrary terms "target" and "probe", or "probe" and "target", respectively, as they are used in other publications.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mnM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions determine whether a nucleic acid is specifically hybridized to a probe. Wash conditions used to identify nucleic acids may include, e.g.: a salt concentration of about 0.02 M at pH 7 and a temperature of about 20° C. to about 40° C.; or, a salt concentration of about 0.15 M NaCl at 72° C. for about 15 minutes; or, a salt concentration of about 0.2×SSC at a temperature of about 30° C. to about 50° C. for about 2 to about 20 minutes; or, the hybridization complex is washed twice with a solution with a salt concentration of about 2×SSC containing 1% SDS at room temperature for 15 minutes and then washed twice by 0.1×SSC containing 0.1% SDS at 37° C. for 15 minutes; or, equivalent conditions. Stringent conditions for washing can also be, e.g., 0.2×SSC/0.1% SDS at 42° C. See Sambrook, Ausubel, or Tijssen (cited below) for detailed descriptions of equivalent hybridization and wash conditions and for reagents and buffers, e.g., SSC buffers and equivalent reagents and conditions.

A specific example of stringent assay conditions is rotating hybridization at 65° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1× SSC at room temperature.

Stringent hybridization conditions may also include a "prehybridization" of aqueous phase nucleic acids with complexity-reducing nucleic acids to suppress repetitive sequences. For example, certain stringent hybridization conditions include, prior to any hybridization to surface-bound polynucleotides, hybridization with Cot-1 DNA, or the like.

Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not especially distinct. In other words, a mixture is not addressable. To be specific, an array of surface-bound polynucleotides, as is commonly known in the art and described below, is not a mixture of capture agents because the species of surface-bound polynucleotides are spatially distinct and the array is addressable.

"Isolated" or "purified" generally refers to isolation of a substance (compound, polynucleotide, protein, polypeptide, polypeptide, chromosome, etc.) such that the substance comprises the majority percent of the sample in which it resides. Typically in a sample a substantially purified component comprises 50%, preferably 80%-85%, more preferably 90-95% of the sample. Techniques for purifying polynucleotides, polypeptides and intact chromosomes of interest are well-known in the art and include, for example, ion-exchange chromatography, affinity chromatography, sorting, and sedimentation according to density.

The terms "assessing" and "evaluating" are used interchangeably to refer to any form of measurement, and include determining if an element is present or not. The terms "determining," "measuring," and "assessing," and "assaying" are used interchangeably and include both quantitative and qualitative determinations. Assessing may be relative or absolute. "Assessing the presence of includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

If a surface-bound polynucleotide "corresponds to" a chromosome, the polynucleotide usually contains a sequence of nucleic acids that is unique to that chromosome. Accordingly, a surface-bound polynucleotide that corresponds to a particular chromosome usually specifically hybridizes to a labeled nucleic acid made from that chromosome, relative to labeled nucleic acids made from other chromosomes. Array features, because they usually contain surface-bound polynucleotides, can also correspond to a chromosome.

A "non-cellular chromosome composition", as will be discussed in greater detail below, is a composition of chromosomes synthesized by mixing pre-determined amounts of individual chromosomes. These synthetic compositions can include selected concentrations and ratios of chromosomes that do not naturally occur in a cell, including any cell grown in tissue culture. Non-cellular chromosome compositions may contain more than an entire complement of chromosomes from a cell, and, as such, may include extra copies of one or more chromosomes from that cell. Non-cellular chromosome compositions may also contain less than the entire complement of chromosomes from a cell.

A "probe" means a polynucleotide which can specifically hybridize to a target nucleotide, either in solution or as a surface-bound polynucleotide.

The term "validated probe" means a probe that has been passed by at least one screening or filtering process in which experimental data related to the performance of the probes was used a part of the selection criteria.

"In silico" means those parameters that can be determined without the need to perform any experiments, by using information either calculated de novo or available from public or private databases.

The term "duplex Tm" refers to the melting temperature of two oligonucleotides which have formed a duplex structure.

The present invention provides alternative and novel microarrays, methods and systems for CGH and location analysis probe microarray selection that overcome the drawbacks of existing microarray probe selection techniques. The methods of the instant invention utilize probe/target hybridization experiments and/or unique data analysis techniques to identify and select nucleotide probe(s) that target polynucleotide fragments from a chromosome of interest. The methods for probe selection described within, will benefit from flexible microarray fabrication technologies that can rapidly customize array content, as more information is forthcoming on which regions of particular chromosomes/genes are important for disease/cancer development as well as disease diagnostics.

The invention provides methods, systems and computer readable media for identifying and selecting nucleic acid probes for detecting a target with a nucleic acid probe array or microarray. The methods comprise, in general terms: the selection of genomic nucleotide ranges of interest, determining appropriate target sequences for CGH and/or location analysis, generating candidate probes specific for the target sequences and analyzing candidate probes for specific probe properties by computational and/or experimental processes to optimize probe selection and reduce the number of probes to a value appropriate for placement on a microarray. The invention also provides microarrays comprising probes selected by the methods of the invention. The microarrays comprise a solid support and a plurality of surface bound probes, the surface bound probes having very similar thermodynamic properties as well as similar GC content. More specifically, a large portion of the probes utilized in the microarrays of the invention, have duplex melting temperatures (Tm) which are within a narrow temperature range compared the Tm range of probes for other microarray systems, such as arrays for gene expression.

The invention is particularly useful with comparative genome hybridization microarrays, such as microarrays based on the human or mouse genome. The invention permits more cost-effective and efficient identification of gene regions or sections which can be associated with human disease, points of therapeutic intervention, and potential toxic side-effects of proposed therapeutic entities.

In general terms, the methods for probe selection and validation of the invention comprise, identifying probe properties that can be determined a priori by the probe's sequence and the sequence of the genome it is contained within, and may further comprise expanding the set of properties from those that can be determined a priori, to those that can be measured empirically through simple experiments, such as self-self experiments. The methods of the invention may further comprise measuring the response of candidate probes to a known stimulus, where the stimulus is generated by a set of samples of where the copy numbers for relatively small subsets of the genome are altered in known ways.

In designing an array comprising high-performance probes that comprehensively covers a whole genome (e.g. the human genome) the entire genomic sequence must be searched when generating specific candidate probes. This homology search is potentially the most time-consuming part of the probe design process. Ideally, a homology search would be the first part of the process, however because of the scale of the human genome executing an exhaustive search of all possible short oligo probes (<100 bases), can take computation time on the scale of a CPU year (based on ProbeSpec), for modern 3 GHz processors. This computation time can be reduced by any of a number of methods, most involving reducing the scale of the search. For example, known highly repetitive sequences can be removed by a process called RepeatMasking. Repeat-masked genomic sequences are publicly available on the web (e.g. UCSC's www.genomebrowser.org). Another approach is to reduce the number of probe sequences being searched up-front. This can be done on the basis of any known property of the probe, from thermodynamic properties, such as duplex-Tm and hairpin free energy, to position on the genome. The present invention provides methods which applies known probe information as a screening process to reduce the number of probe sequences to be analyzed in a homology search, thus reducing the computation time needed to identify appropriate probes for a CGH based array.

The present systems, techniques, methods and computer readable media also provide for streamlined workflow, since researchers need only to prepare and process one microarray instead of two or more per sample, with fewer steps in processing and tracking required.

Further, greater reproducibility of results is provided for, since all data for an entire genome is generated from a single microarray, resulting in less variability in the data. When two or more microarrays associated with the same sample are processed separately, there are always questions of variability of the experimental conditions used to process each microarray.

Designing a microarray involves determining the amount of "real estate" (number of probes) that is available for the final array. The array designer also determines the amount of probes or "real estate" to use for specified regulatory regions, intergenic regions as well the amount of probes necessary to adequately cover introns and exons of the chromosomes of interest. Initially, a designer will generate 20 to 40 million candidate probes and need to filter the probes for certain probe properties or parameters to obtain a final array with approximately 40,000 probes. Intermediate arrays are manufactured in some embodiments of the methods of the invention, which have a redundancy of 3 or 4 fold over the number of probes selected for the final array, these intermediate arrays are utilized to screen candidate probes for certain probe properties by direct or indirect experimentation.

In many embodiments, the oligonucleotides (i.e. probes) contained in the features of the invention have been designed according to one or more particular parameters to be suitable for use in a given application, where representative parameters include, but are not limited to: length, melting temperature (Tm), non-homology with other regions of the genome, hybridization signal intensities, kinetic properties under hybridization conditions, etc., see e.g., U.S. Pat. No. 6,251,588, the disclosure of which is herein incorporated by reference.

Standard hybridization techniques (using high stringency hybridization conditions) are used to probe subject array. Suitable methods are described in references describing CGH techniques (Kallioniemi et al., Science 258:818-821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Galla et al. Meth. Enzymol., 21:470-480 (1981) and Angerer et al. in Genetic Engineering: Principles and Methods Setlow and Hollaender, Eds. Vol 7, pgs 43-65 (plenum Press, New York 1985). See also U.S. Pat. Nos. 6,335,167; 6,197,501; 5,830,645; and 5,665,549; the disclosures of which are herein incorporate by reference.

Referring now to FIG. 1, there is shown a flow chart of events that may be carried out in a nucleic acid probe selection method in accordance with the invention. At event 10, a nucleotide sample is selected for probe design for microarray analysis. The nucleotide sample may be a genome or genomic nucleotide range or ranges, such as a chromosome. At event 20, potential target sequences of the nucleotide sample of interest are identified, filtered and reduced to a set of appropriate target sequences for CGH and/or location analysis. The potential target sequences are filtered by size, number of repeat-masked bases and/or GC-content. Target sequences are also filtered and reduced in number by eliminating repetitive target sequences in event 20. Another parameter which can be used to filter target sequences, is to eliminate potential target sequences which comprise a restriction enzyme cut site. By limiting the size of the set of target sequences, the computational time needed to generate and analyze the candidate probes is decreased. These and other processes involved in obtaining appropriate target sequences for CGH probe selection are more fully described in FIG. 2 below.

After determining a set of appropriate target sequences in event 20, candidate probes to the genomic sequence (e.g. chromosome) of interest are generated at event 30 as shown in FIG. 1. Generating a set of candidate probes comprises tiling probes across regions of the target sequences determined in event 20, which enables the candidate probes to be free of repeat-masked section as well as restriction cut sites if desired. The generation of candidate probes may comprise additional filtering and reduction depending on the genomic sequence of interest.

At event 40, the candidate probes are filtered or reduced in total numbers by utilizing indicators or metrics of certain probe properties which assess candidate probe quality in silico. In silico means those parameters that can be determined without the need to perform any experiments, by using information either calculated de novo or available from public or private databases. Probe parameters utilized to annotate candidate probes may include but are not limited to target specificity, thermodynamic properties, expression and association with genes, homology and also kinetic properties. The annotation of candidate probes in silico, by these and other probe properties are more fully described in FIG. 3 below. Candidate probes which do not meet the in silico parameters or indicators for a "good" probe are discarded from the probe selection process at event 42.

Figure 6:
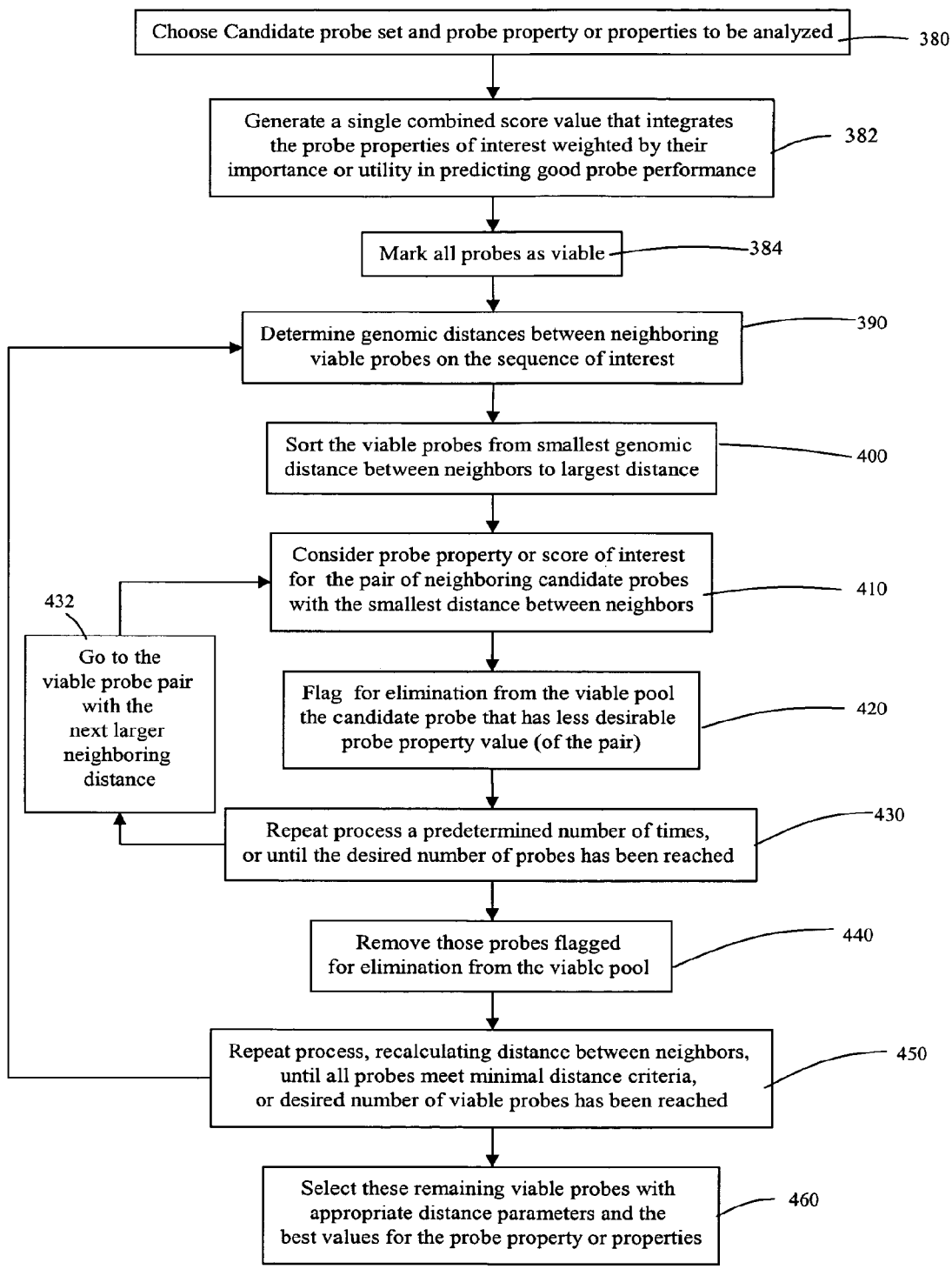
FIG. 6 is a flow chart of a pairwise process for analyzing candidate probes for CGH arrays in accordance with the invention.

Candidate probes which are identified to have certain desirable probe properties in silico, are subjected to a pairwise selection process to filter and reduce the number of potential probes at event 50. The pairwise filtering evaluates a pair of candidate probes for a probe property or set of property and scores the probes within the pair against each other according to the probe property analyzed. FIG. 6 describes in more detail the process for pairwise filtering. Probes which do not pass the pairwise selection process are not selected and are discarded in event 52. Probes which pass pairwise filtering may require further filtering and can be evaluated experimentally for other desirable probe properties at event 60. In certain embodiments, selecting probes for a CGH or based array requires no further filtering or reduction of candidate probes besides for those applied by the pairwise and in silica analysis as shown in event 54. As more indicators and metrics for probe performance are identified and adapted for analyzing probe performance in silico, less emphasis is placed on experimental probe results for CGH probe selection.

In the method shown in FIG. 1, candidate probes which meet the pairwise filtering may require further analysis by measuring specific "good" probe indicators/probe properties experimentally at event 60. To obtain a sense of a probe's performance, experiments are completed which measure properties of a probe that can, in the absence of more direct experiments, provide a good indication if a probe will be suitable for a CGH or location analysis array. Such experimentally measurable properties useful in determining a candidate probes performance include but are not limited to; raw signal intensity, reproducibility of signal intensity, dye bias, and susceptibility of non-specific binding. These empirically determined probe indicators as wells as others, are described more fully in FIG. 4 below.

Candidate probes which do not meet the experimentally measurable probe parameters are discarded/unselected in event 70, while the remaining candidate probes which meet the probe parameter standards in event 60 may be utilized for CGH arrays, event 72 or be subjected to further filtering by completing probe validation experiments at event 80. The order in which experimentally measurable probe parameters are applied to candidate probes may vary depending on the genomic sequence of interest.

At event 80, candidate probes are placed on an array and subjected to target sets/samples comprising known target sequences with known copy numbers. The probes are evaluated and scored by assessing a plurality of probe properties over numerous target sets. The details of the probe properties and the methods utilized in probe validation experiments are described in more detail in FIG. 5 below.

The candidate probes are evaluated in event 80 for adequate signal response as well as reproducibility across target sets. The candidate probes which obtain a high validation score from the validation experiments are suitable for use on a CGH array, event 72, while candidate probes with deficient or poor validation scores are not selected in event 90.

Depending on the space available on the array chip, more or fewer probe parameters can be implemented and/or the thresholds and cut-offs of probe parameters may be adjusted as needed. Candidate probes may be prioritized, for example gene-by-gene, region-by region, or strictly filtered on validation scores. Also annotation of probes for position, gene association and expression may also be utilized to finalize the probe selection for a CGH or location array.

Figure 2:
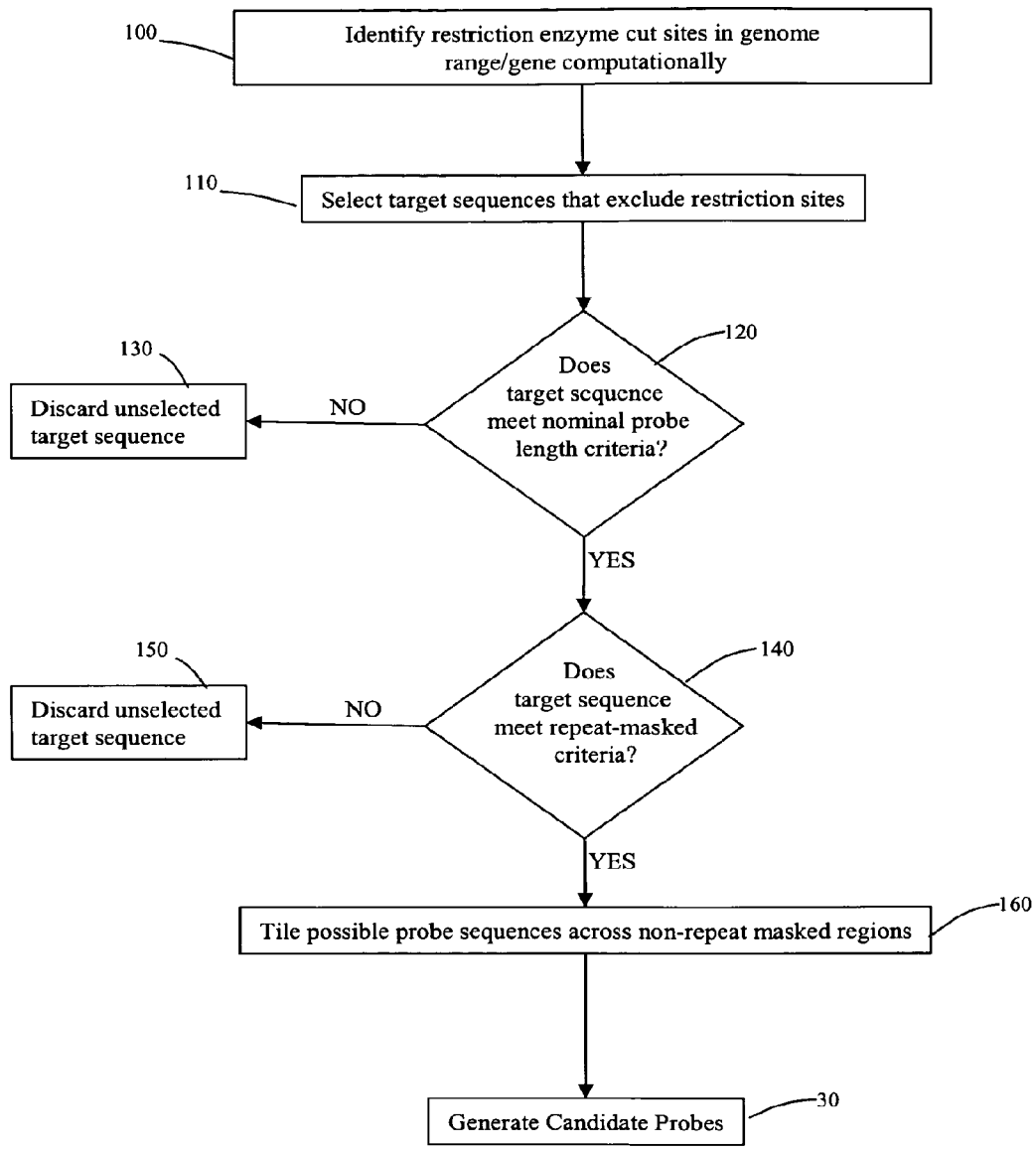
FIG. 2 is a flow chart of a process for filtering and reduction of target sequences in accordance with the invention.

Referring now to FIG. 2, there is shown a flow chart of one embodiment of the invention, showing the events for identifying and filtering potential target sequences. At event 100, the genome range (e.g. a chromosome) of interest is analyzed by a process which identifies potential cut sites for various restriction digest enzymes. Many scientist utilize restriction enzymes in CGH experiments to produce poly-nucleotide fragments from target samples, thus in some embodiments it is preferable to eliminate probes with restriction enzyme sites from the probe selection process. While event 100 is optional in certain embodiments of the methods of the invention, it can be a useful filtering tool which decreases the computational time needed to analyze candidate probes as well as a desired feature by some scientist. Exemplary restriction enzymes which can be utilized in a CGH protocol are RSA1, Alu1. Screening the chromosome of interest for restriction sites allows for the filtering and reduction of potential target fragments which occurs in event 110. Target sequences which include a restriction cut site are eliminated from the set of potential target fragments which are the basis for generating CGH probes. Reducing the number of potential target fragments at an early event in the methods for CGH probe selection, enables less computational power and time to be needed in identifying optimal CGH probes.

In the embodiment shown in FIG. 2, potential target sequences excluding restriction sites are further evaluated to determine if they meet certain criteria for nominal probe length in event 120. Potential target fragments are evaluated for appropriate length, for example those shorter than e.g. 60 base pairs are not considered initially and fragments with length greater than 800 base pairs are also put aside. The length cutoff parameters may be adjusted depending on many factors, for example, number of potential target fragments, characteristics of the genomic range of interest, dependence of hybridization rate on target length, processivity of labeling enzymes, and visual inspection of longer target sequences for repetitions.

Those target fragments which do not meet the length criteria are discarded or put aside in event 130. It should be noted that these target fragments maybe revisited at a latter time in the method of selecting CGH probes if it is determined that cutoff or threshold for target fragment length needs to be adjusted.

Potential target fragments may further be filtered by excluding target fragments containing repetitive sequences in event 140. RepeatMasker, a software program, is another useful tool in eliminating regions of the genomic sequences from becoming potential target fragments because they are known repetitive sequences. RepeatMasker uses a database of known sequences and algorithms to determine repetitive sequences in order to mask them in any sequence. Those target fragments which do not meet the non-repeat mask criteria are discarded or set aside in event 150. Again, by filtering out and reducing the number of target fragments at an early event in methods for CGH probe selection, the computational time to evaluate specific probe parameters at latter events is reduced significantly.

In event 160, the target fragments which have met the criteria for repeat masked and nominal probe length are subjected to probe tiling. Probe tiling comprises computationally producing candidate probe sequences from the sequences of the target fragments. An arbitrary probe length is determined or chosen and the target fragment sequences are divided into segments having the specified probe length. For example, if a probe length of 60 base pairs is chosen, the non-repeat-masked regions of target fragments are tiled in steps of 30 bases to produce candidate probes in event 30. The probe tiling procedure starts a new probe at the first non repeat-masked base within a target fragment sequence, when a repeat-masked section is encountered, the sequence is skipped and the tiling process restarts at the next non-repeat masked base. The probe length and/or tiling step size may be altered to allow for more relaxed or stringent parameters for candidate probe generation.

Figure 3:
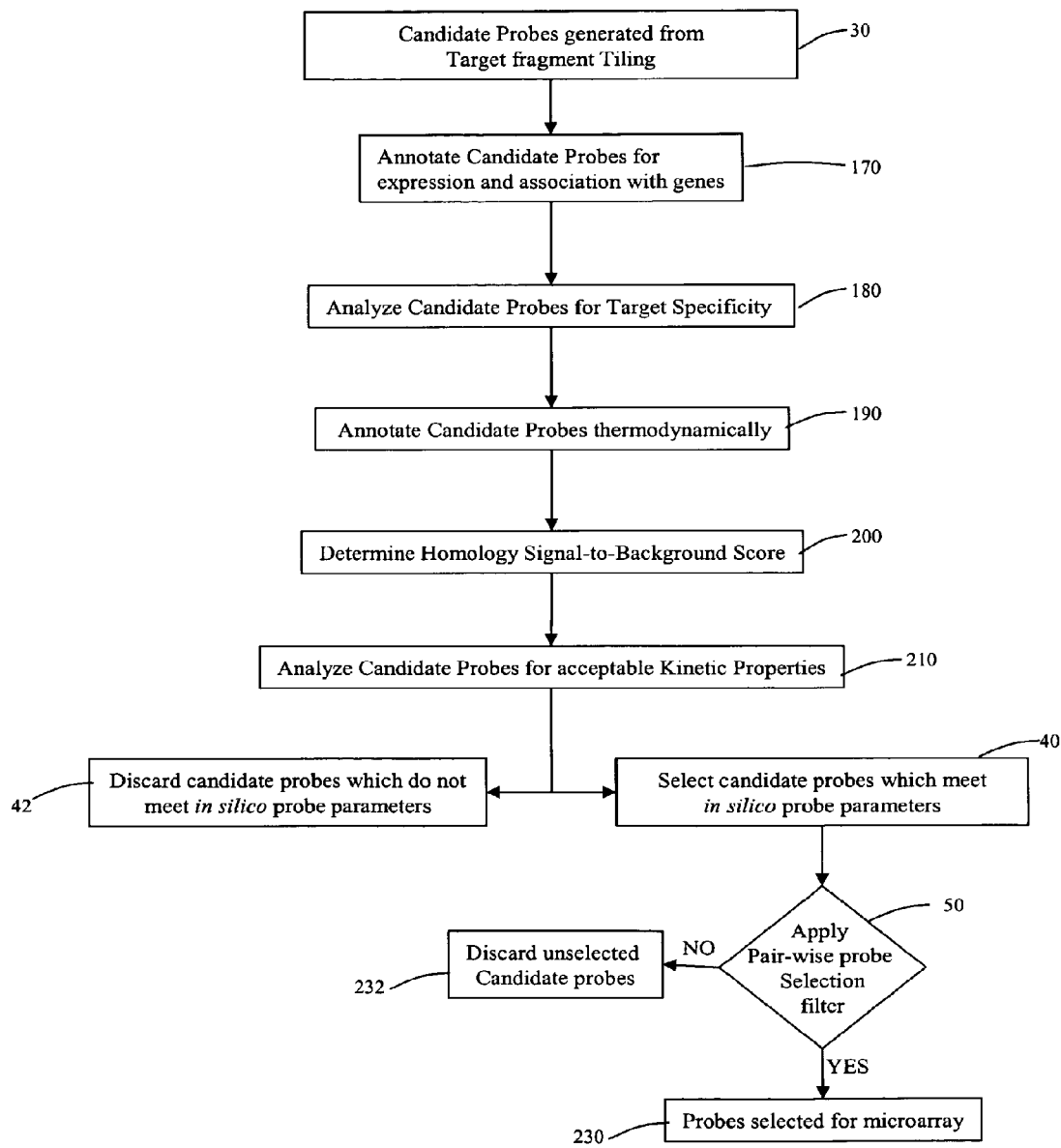
FIG. 3 is a flow chart of a process for analyzing candidate probes in Silico for selecting probes for CGH arrays in accordance with the invention.

The use of certain probe properties as in silico indicators for "good" probes allows the reduction of the total number of viable candidate probes. Referring now to FIG. 3, a flow chart is shown depicting one embodiment of the methods for analyzing candidate probes by certain probe properties in silico in accordance with the invention. Candidate probes generated from target fragment tiling in event 30, are subjected to annotation for expression and association with genes at event 170. In this event, a number of databases are utilized to determine probe sequences that are contained within introns or exons of either known genes or predicted genes. This process involves accessing the message alignments to genomic sequences, and determining whether the probes are either partially or wholly contained within the confines of the exons of the messages.

The utility of this process allows the operator to arbitrarily choose the densities for the homology searching of intronic probes (probes within introns), exonic probes (probes within exons), and intergenic (probes between genes) probes. The candidate probes may be annotated independently for whether they are in expressed intron regions or within the bounds of a message or within a "premRNA".

In event 180, candidate probes are analyzed for target specificity. Specificity is the measure of the incidences of target sequences complementary to, or nearly complementary to a candidate probe. Complementary refers to a sequence that can form a duplex that is Watson-Crick base-paired (or analogously paired by virtue of all possible nucleotide analogs and generic bases) to another sequence within the genome. "Nearly complementary" means that the sequences are complementary enough to form moderately stable duplexes, though some small number of bases are not Watson-Crick base-paired, due to mismatches, insertions, or deletions of bases in one sequence relative to the other.

By comparing the sequences of candidate probes to the entire genomic sequence, the specificity of the probes to their respective targets in the hybridized solution can be calculated. This is possible for human, mouse, rat and other species where the genomes have been sequenced either completely or nearly so.

Tools and methodologies to determine specificity include, but are by no means limited to: BLAST® (Basic Local Alignment Search Tool), MegaBLAST, BLAT (BLAST-like Alignment Search Tool), ProbeSpec, RepeatMasker.

BLAST, MegaBLAST, and BLAT are tools widely used for genomic and expression sequence analysis. They are all used to find sequences within a sequence data set (the genomic sequence for the organism of interest) that are similar to the query sequence (in this case, the probe sequence) to within some minimal number of matching bases. Each genomic sequence found that is similar to the intended target sequence the position and match properties, such as match start and stop positions, numbers of insertions and deletions, etc., is scored as a "hit". Each hit is recorded as a separate record to an output file. MegaBLAST is quite similar to BLAST, and uses similar underlying algorithms, optimized for aligning sequences that differ slightly as a result of sequencing or other similar "errors". MegaBLAST can run many times faster than BLAST, depending on the size of the candidate probes sequences. BLAT differs from BLAST in that it is designed for transcript alignment, so multiple alignments of a single transcript to a finite region of the genome are returned in a single record.

BLAST and MegaBLAST have the disadvantage that any non-specific probe can generate a large number of "hits", each hit resulting in a separate record in the output file produced. This means that where probes are highly nonspecific, the output file can potentially become quite large. Although it is possible to limit the number of records produced, it's sometimes quite useful to know how many hits were found. As a result, a separate tool with a fast file parser, is then necessary to take the BLAST results file and process it to generate a histogram of hits, a specificity score or specificity classification for each candidate probe. The use of ProbeSpec avoids this problem.

ProbeSpec, a COM-object, is well-suited for designing and selecting probes for a CGH array since rather than keeping information pertaining to every hit for each probe, this program retains only the histogram of the "distances" of each hit relative to the query (or probe) sequence as well as the information for the nearest match and the first exact matching sequence. The term "distance" refers to the number of base differences between the probe and a close target sequence in the background (other genomic stretches in the sample mix). ProbeSpec provides sufficient candidate probe information for the probe design process, without additional extraneous data. ProbeSpec reports the number of exact hits for each candidate probe, and also the distributions of the closer set of sequence matches up to some arbitrarily predetermined distance.

It should be noted that the number of mismatched, inserted, or deleted bases that must be considered (searched for and counted) in the homology search, depends on the length of the intended probe, the destabilizing effect of the mismatches on the duplex stability, and the stringency of the conditions of the hybridization reaction. Typically, for longer probes more mismatches must be considered. For example, a reasonable minimum number of mismatched bases to consider for 30-mer probes is 7, whereas for 60-mer probes 15 or more mismatches should be considered.

At event 190, the candidate probes are annotated thermodynamically in silico. Thermodynamic parameters associated with duplex stability, target structural stability, and probe hairpin stability are utilized to evaluate the candidate probes. Duplex stability is the stability of the duplex formed between the probe and its target. Target structural stability evaluates the stability of secondary structure within the target sequence. Probe hairpin stability is the stability of secondary structure within the probe sequence. The presence of stable secondary structure interferes with the ability of the target to hybridize with the probe. The thermodynamic parameters utilized to annotate candidate probes include but are not limited to, melting temperature ($T_m$), entropy ($\Delta S$), enthalpy ($\Delta H$), and Gibb's free energy ($\Delta G$) values. Candidate probes may also be analyzed for base content, i.e. GC-content, which gives a good estimation of Tm for longer candidate probes.

At event 200, candidate probes are evaluated for homology signal to background and scored accordingly. The target specificity of a candidate probe is related to the homology of the probe with respect to the rest of the genome, as described above. Homology search results are reported by ProbeSpec as a histogram of hits at various distances, rather than as a single record per hit, as is typically done by BLAST. The homology properties for a candidate probe can be evaluated or defined by a single parameter, the Homology-Signal-to-background or HomS2B parameter, or when the HomS2B parameter is expressed on a log scale (defined below) HomLogS2B. The results from ProbeSpec can be processed to generate a homology Signal to Background (HomLogS2B) score for each candidate probe. The HomS2B parameter utilizes a plurality of homology information on candidate probes to generate a theoretical signal to background score for each probe, where the signal is defined to be the signal obtained from a single specific perfect match target (i.e. 100% homology), and the background is the superposition of all the non-specifically binding targets from the complex mix of the whole genome, or the amplified or reduced complexity mix that may be present in the case of a complexity reduced assay.

A sample or target mixture with reduced complexity is one in which certain regions of the Genome are either selectively amplified or regions of the genome are physically separated from other regions. The use of reduced complexity target mixtures diminishes the level of stringency required for the hybridization to be effective.

Calculating a HomS2B score utilizes a simple approximation of the homology histogram of distances to generate the equivalent signal from an ensemble of targets competing with the probe. This is estimated by the following formula:

$$HomS2B \equiv \frac{S}{B} \approx \frac{N_t}{(N_0 - N_t) + \sum_{d=1}^{D} P_d N_d}$$

where $N_d$ represents the histogram of homology hits at each distance d, where d is defined as the number of single-base differences between a target and the probe.

$N_t$ is the number of copies of intended targets. Two duplicated regions in close proximity on the same chromosome (which occurs frequently) may be a viable example of where we would intentionally design probes complementary to more than one target. $P_d$ is the signal penalty associated with the distance, d. The penalty, though given here as dependent only on the mis-match number (or "distance"), it may be associated with the number of mismatches, the position of the mismatches, the base composition and orientation of the mismatch, and the nature of the mismatch (base-insertion, base-substitution, or base-deletion). This is an approximation of the homology histogram of distances because the precise penalty is a function of the sequences of both the target and probe sequences for all near matches under consideration. The approximation is based on the assumption that the average signal reduction across a large number of probe-target mismatches is a reasonable representation for any given mismatch of the same order. This approximation of the homology histogram of distances can be either theoretically or empirically determined. The type of mismatch and distributions of sequence mismatches affect the exact penalty given. For example, single-point insertions and deletions of 5 bases are generally less destabilizing than 5 single-base mismatches that are evenly distributed across the duplex. Or for that matter, the distribution of mismatches across a duplex will likely cause substantial variations in the penalty as well. The approximation of the homology histogram of distances may further comprise an additional step, which assumes a constant penalty P for each base-distance. In this case, the approximation $P_d \approx P^d$ is used.

Typically, the numerator, $N_t$, is unity as in most cases there is a single copy per chromosome of each target we are probing. The denominator includes a term representing the unintended target regions that are exactly complementary to the probe. The first $N_t$ intended targets are represented in the numerator, whereas all other exact copies are in the background, since they are not the intended targets.

The HomS2B parameter can be conveniently represented as a log normalized to the penalty per base, as shown in the following formula:

$$HomLogS2B \equiv \frac{\log\left(\frac{S}{B}\right)}{\log(P)}$$

HomLogS2B expresses the signal to background score for a probe in units commensurate with distance from the nearest hit. That is, if there is a single perfect match intended target to the probe of interest, no unintended perfect match targets, and a single significant background target at a distance of d, HomLogS2B will equal –d.

Another approach to calculating the Signal to background score is to calculate the Duplex Tm between the probe and each and every potential cross-hybridization competitor during a homology search.

At event 210, the candidate probes are analyzed for kinetic properties. Because the arrays are generally hybridized to their targets for a time less than that required to reach thermodynamic equilibrium, the observed signals from hybridized targets depends on the rate at which they hybridize, as well as on the thermodynamic stability of the duplex. Some targets, because they are exceptionally long or contain secondary structure, hybridize significantly more slowly than others, and are therefore less desirable targets to probe. Kinetic properties of targets can also be measured and evaluated empirically, in event 60 as further discussed below.

In silico properties which are very effective for eliminating unacceptable probes are probe homology (HomLogS2B) and duplex-Tm, with hairpin free energy values. Probes which meet the in silico parameter(s) are selected in event 40 and those probes which do not meet the in silico parameter(s) are discarded or de-selected in event 42.

At event 50, candidate probes selected at event 40, are subject to a pairwise selection process using an algorithm(s) which evaluates candidate probes by both the region of the genomic range of interest that they target and a specified probe property or characteristic (e.g. $T_m$). Candidate probes which pass the pairwise selection process are selected for a microarray in event 230. Probes which do not meet the pairwise criteria are discarded in event 232. The pairwise probe selection algorithm(s) reduces the number of probes associated with a given region of the genomic range of interest while weighting probe selection towards a preferred parameter value. The method of applying pairwise probe selection to candidate probes is more fully described in FIG. 6 below.

Candidate probes may be further subjected to a biased pairwise selection process which uses an algorithm(s) which evaluates candidate probes by pairwise selection and these results are biased by a different probe characteristic. For example, two properties are analyzed during pairwise selection, e.g. the region of the genomic range of interest that the candidate probes target and a specified probe property or characteristic such as homology score, followed by results evaluating or biasing the results with another probe parameter, such as $T_m$. The biased pairwise probe selection algorithm(s) reduces the number of probes associated with a given region of the genomic range of interest while biasing probe selection towards a preferred parameter value. The method of applying biased pairwise probe selection to candidate probes is more fully described in FIG. 7 below.

Figure 4:
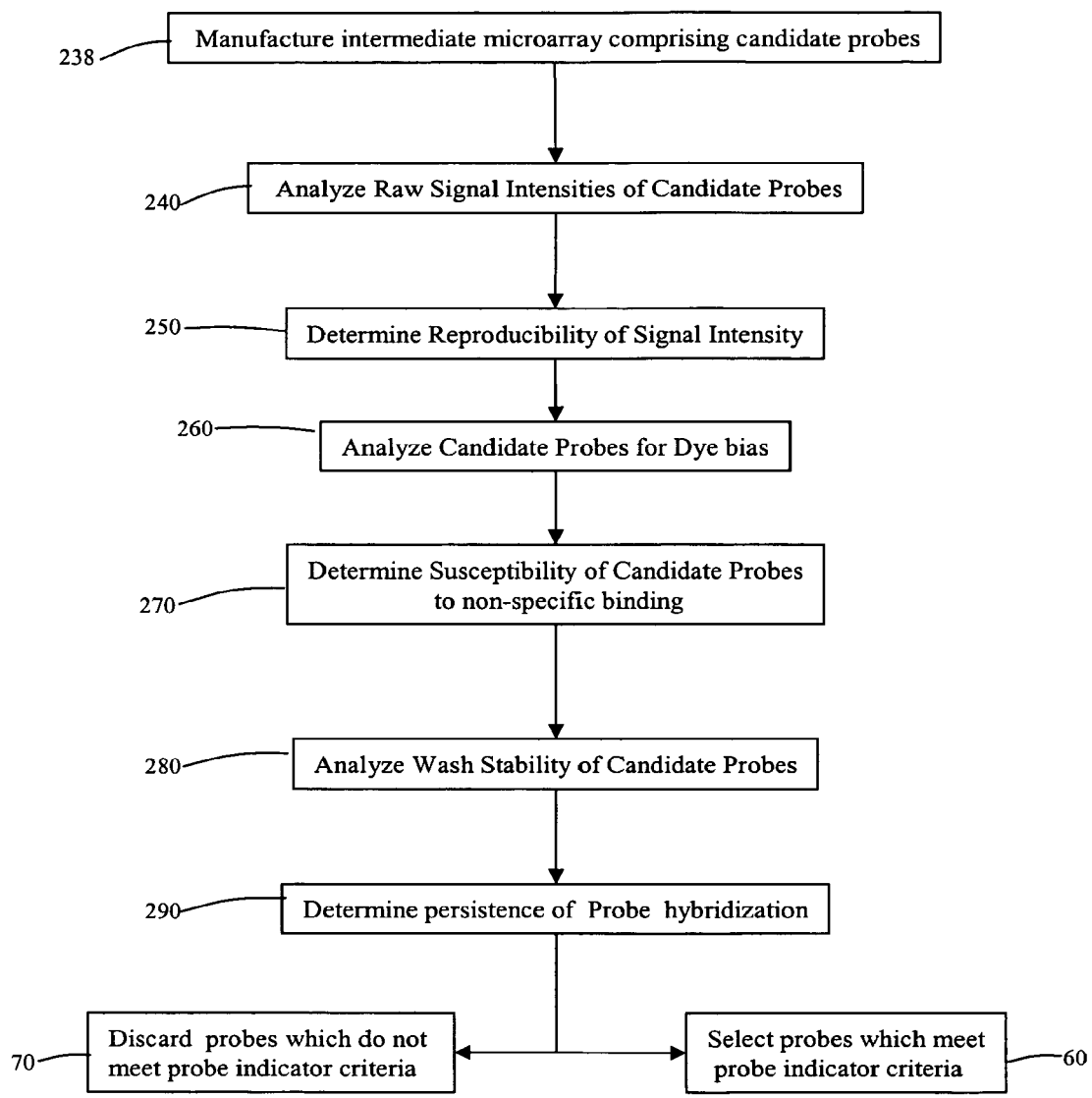
FIG. 4 is a flow chart of a process for analyzing candidate probes utilizing empirically determine probe indicators for selecting probes for CGH arrays in accordance with the invention.

Referring now to FIG. 4, there is shown a flow chart of the process in determining probe properties of candidate probes empirically. In general, a plurality of indicators for probe performance can be empirically determined for candidate probes, using samples whose relative copy numbers of complementary genomic sequences are equal. Any sample, when hybridized with the same sample as a reference, can serve for this level of empirical validation, whether the relative copy numbers of genes within the sample are known or unknown. The preferred samples to use for validation, however, are normal diploid cells, for which the copy numbers of all targets are equal. These types of experiments are sometimes called "self-self experiments".

At event 238, the selected candidate probes are placed on an "intermediate" or test array for experimental analysis. At event 240, the candidate probes are analyzed for raw signal intensity. Raw signal intensity is the background-subtracted signal, without normalization, reported for each feature in each channel scanned.

The signal strength of a candidate probe is an effective indicator of probe performance. While some experimentation is necessary to measure signal strength, the experimentation does not require an independently variable set of targets. A probe's signal, in the absence of and actual target number change, is thought to be related to target specificity a priori, since the more non-specific a probe is the more unwanted targets will bind to that probe. For a set of probes selected to have the same melting temperature (or narrow range of melting temperatures), where each specific target molecule is labeled with a single label molecule, such as with end-labeling methods, all probes should have approximately the same specific signal. For other labeling methods, the number of label molecules on the targets can vary, so that the specific signal of a probe for a normal diploid sample also varies. However, if probes are chosen for targets within narrow ranges of sequence length and similar base composition, a moderately narrow range of signal strengths for specific probes is usually observed.

Besides direct binding of non-specific targets, another source of non-specific binding which contributes to excessive signals is so-called "sandwich cross-hybridization". Since the targets are, in general, longer than the 60-mer probes, the probe-target duplexes often have dangling ends of single-stranded target. If the probe itself is specific to its respective target in one region of the target, but the target is non-specific in one or more other regions, then the target will bind many other labeled targets, and attach those indirectly to the probe. An increase in signal is seen relative to the signals of specifically bound probe-target duplexes. Probes subject to sandwich cross-hybridization can be screened in silica, or selected against in empirical validation event 240.

At event 250, the reproducibility of signal intensity is determined for candidate probes. The reproducibility of signal intensity is obtained by analyzing a number of different samples, with differing cell types, separate amplification, digestion, and labeling reactions, on different days, and measuring the variation if signal intensity after hybridization. Some probes are more sensitive than others to small variations in sample preparation conditions, and those probes are eliminated in this event. The more varied the samples and experimental conditions the more robust the performance of the validated probes.

At event 260, the candidate probes are analyzed for Dye bias for two-color measurements. When identical samples are labeled with different fluorometric labels, and hybridized together (a "self-self" experiment), the log ratios of signals in the two channels can differ from zero either due to random variation, or because targets containing one label amplify, label, or hybridize more efficiently than targets containing the other label. This systematic difference between the signals from identical targets containing different labels depends in complex ways on the probe sequence. Probes that are particularly susceptible to dye bias are identified by their reproducible deviations from zero log ratios in replicate self-self experiments. Such probes are eliminated in event 260.

At event 270, candidate probes are analyzed for susceptibility to non-specific binding. A probe's susceptibility to non-specific binding is indirectly determined by the signal strength of the probe. Non-specific binding may also be determined in direct validation experiments as described in other events.

At event 280, the candidate probes are analyzed for stability during hybridization wash conditions. A relatively stringent wash step is necessary to remove undesired targets that are only weakly homologous to the intended target (and which therefore are not rejected by the homology search score in event 220), but which are sufficiently abundant in the genome that appreciable numbers of hybrids are formed. The wash is, however, not so stringent that it dissociates duplexes with the desired complementary targets to a significant degree. Therefore, if the slide is rewashed and rescanned, the signals should not change significantly, since the non-specific targets have already washed off in the first wash, and the specific targets don't wash off. Some probes, however, either bind unusually tightly to non-specific targets, or bind less strongly to their intended targets, so that their signals continue to decrease when rewashed. These probes are eliminated in event 280.

At event 290, candidate probes are analyzed for "persistence". Persistence is an alternative measure of non-specific binding and is defined as the ratio of intensity signals at long hybridization times, to intensity signals at short times. A persistent probe is one which hybridizes steadily, following a bimolecular rate law. Non-persistent probes show a rapid increase of signal at very short times, followed by a slow increase according to the usual kinetics. Persistence is a parameter/value which is complementary to the wash stability test of event 280. Persistence is measured by hybridizing the same sample to replicate arrays for two or more different lengths of time, usually one fairly short time (e.g. one hour) and one more typical time (e.g. 24 hours). Probes which show an excessive degree of prompt binding are eliminated in event 290.

The metrics for nonspecific binding presume that nonspecific signal arises from a large number of weakly-bound sequences, which can be selectively removed in stringent washes, and which bind more rapidly (due to their high concentration) but dissociate more quickly (due to lower binding constants) than the perfectly complementary targets of interest.

Important probe performance indicators, which are determined empirically, are reference (normal sample) signal intensity, dye bias, wash stability, and persistence. At event 60, candidate probes are selected or give high performance scores if they meet the criteria set by the empirically measurable probe performance indicators utilized in event 240, 250, 260, 270, 280 and 290. Candidate probes which do not meet these criteria are not included in final CGH/location analysis probe selection at event 70.

Candidate probes which are rejected or discarded from the selection process of the methods are more appropriately considered as probe outliers. Candidate probe outliers are defined by population statistics, involving means, standard deviations, mediums, interquartile ranges and the like, and are rejected based on one or a combination of probe properties mentioned above. Outliers include but are not limited to probes which are in the outer edges of a probe property distributions, that may exhibit compromised performance.

Figure 5:
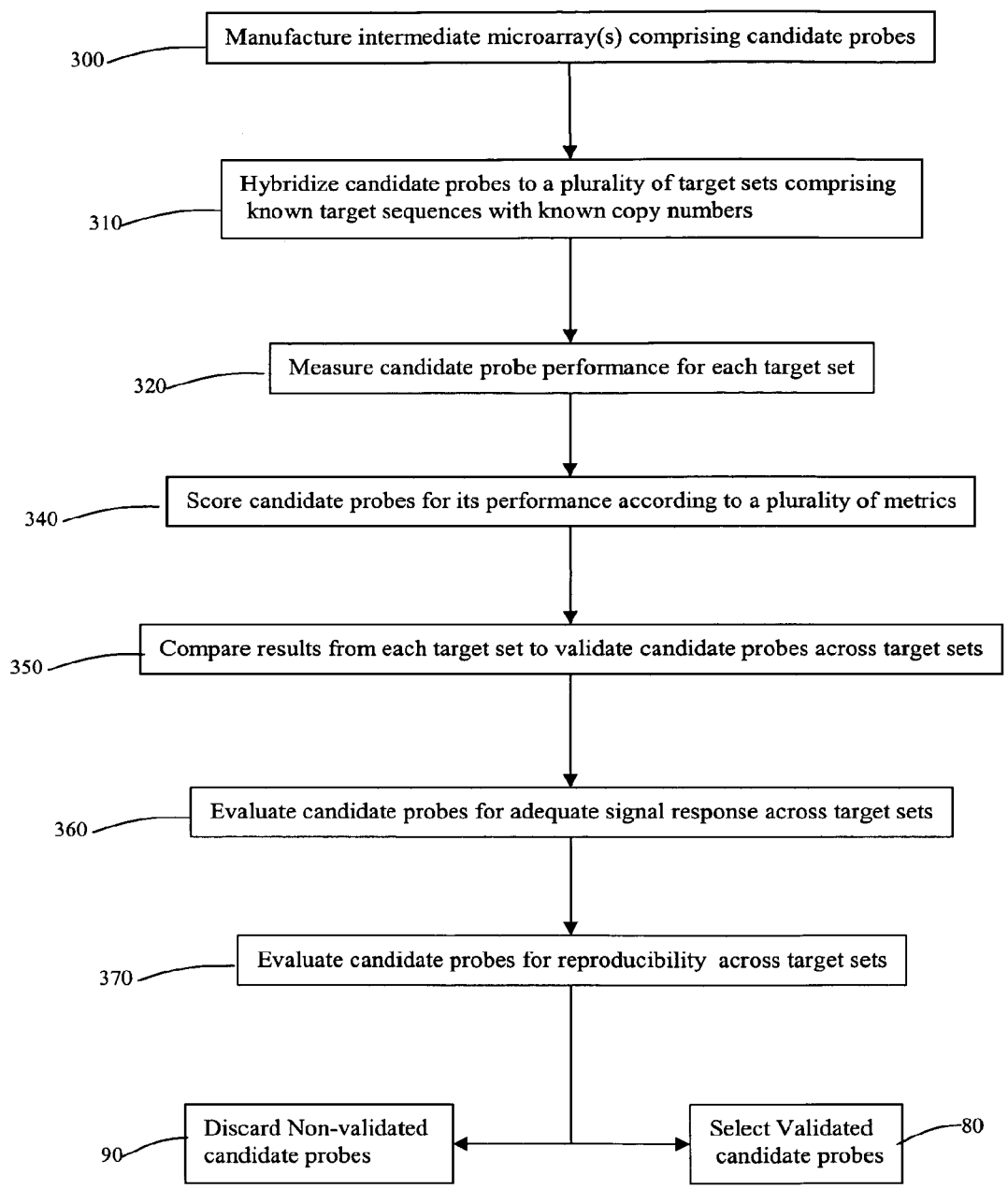
FIG. 5 is a flow chart of a process for validating candidate probes by target hybridization experiments for selecting probes for CGH arrays in accordance with the invention.

Referring now to FIG. 5, there is shown a flow chart of events useful in determining probe properties of candidate probes directly by experimentation. Direct measurement of probe performance, is determined by validation experiments using samples whose relative copy numbers of complementary genomic sequences are known a priori. At event 300, candidate probes, which have desirable probe properties determined in silico and/or empirically, are laid out on a prototype array. In certain embodiments, it may be useful to proceed with direct experimentation with limited or no in silico or empirical prior data. The candidate probes are placed on the array using array techniques known to those skilled in the art of microarrays. Array layout protocols include randomization, periodic grid tiling, text-ordered tiling, and serpentine tiling. By making prototype "intermediate" arrays with more probes for a given region of the genomic range of interest, than would be placed on a final array design, those probes that behave best according to some set of metrics for probe performance for that particular region can be selected.

At event 310, the candidate probes on the array are hybridized to various target sets comprising known target sequence with known copy number. A target set comprises a quantity of target molecules within the mixture that is deterministically altered, or known to differ in a well-defined way from that of a "normal" target set sample. A plurality of arrays are utilized to test various probe properties for the plurality of target sets.

In general, all subsets of the target sequences are altered in copy number (or deleted altogether) without dramatically altering the composition of the rest of the genome. For example, two normal tissue samples, one from a male tissue or cell line, and another from a female can be analyzed. Both will have the same number of target sequences for each region of every chromosome (notwithstanding the usual polymorphic variations) except the X-chromosome and the Y-chromosome. The male sample has a single copy of the X and Y chromosomes, whereas the female will have two nominally identical copies of the X-chromosome. So the male sample will have ½ the number of copies of the X-chromosome as does the female sample, and the female sample will have no copies of the Y-chromosome targets. Probes for targets on the X-chromosome should display, after normalization, twice as much signal for the female sample as for the male sample. The fractional increase in the log base 2 of the observed signal for a probe, when the copy number of its intended target is doubled, is the "slope" of that probe. Ideally, probes should have a slope of 1.0. Probes with significantly and systematically different slopes are inferior performers, and are issued low "differential response" scores. The same approach can be used with cell lines of known chromosomal copy number variations, where they can be found. It is unlikely that cell lines with alterations spanning the whole human genome can be derived from naturally occurring variations (e.g. diseases). With such a set of samples, multiple measurements analogous to those of male to female signal ratios for each probe can be obtained.

Also, when the known copy number of a particular target sequence in a sample is zero (as, for example, Y-chromosome probes in female samples), any signal observed for that probe must result from cross-hybridization. Probes that show significant signal for samples in which their known copy number is zero are scored low on the "cross-hybridization" score.

At event 320, the candidate probes are measured for probe performance for each target set. The results of the hybridization experiment are analyzed for a plurality of probe performance indicators which may include but are not limited to, slope of response curve (a differential response score), cross-hybridization, Y-axis intercept of response curve (equivalent to dye bias), reproducibility or noise, P-value of separability of distributions based on repeated measurements at two or more target copy number values, variance of signals, and variance of ratios.

At event 340, candidate probes are scored and/ranked according to the various indicators or parameters for probe performance. The candidate probes are scored for each target set tested.

At event 350, the experimental results obtained from each target set for each candidate probe, are compared to validate candidate probes across target sets.

At event 360, the candidate probes are evaluated for adequate differential response across target sets. For example, probes may be chosen that give the slope closest to the theoretical slope for the set of samples. This is accomplished by simple filtering, such as by selecting a range of tolerable ratios, or by using a more complex algorithm that uses the ratio information in conjunction with other probe information.

At event 370, candidate probes are evaluated for signal reproducibility across target sets. Signal reproducibility is determined in the same manner as with the self-self validation experiments described in event 250.

At event 80, candidate probes which have been validated by the probe metrics determined experimentally are passed to the next step of the selection process or may be selected for placement on a CGH array. Candidate probes which are not validated are discarded at event 90.

Often during probe design, far more candidate probes are generated than the number of probes that are actually needed to cover a given region or a given gene. Generally, it is desired to have uniform spatial coverage over the chromosome, or over some region of interest. However, there are other parameters other than spatial coverage that are desirable, which are used to bias probe selection. For example, where there are more candidate probes than resources to search with, probes may be sacrificed according to other parameters. With the knowledge that probes with lower $T_m$'s often behave better than high-$T_m$ probes, candidate probes in a certain region of interest may be analyzed or biased by duplex-$T_m$ probe values. The pairwise probe-selection allows for the filtering of candidate probes within a region of interest by a specific probe property.

Pairwise filtering is utilized in some embodiments to filter candidate probes to generate probe sets for intermediate arrays. The pairwise filtering is used on candidate probes within genes (on a gene-by gene basis) to reduce the number of probes per gene to a small reasonably uniformly spaced set, while simultaneously selecting higher scoring probes based on in silico parameters, and perhaps also biasing (biased pairwise filtering) these results for whether the probe is in an exon rather than an intron.

Pairwise filtering is also useful in identifying probes within intergenic regions to provide a somewhat uniform coverage between genes. The target density across intergenic regions may be set prior to pairwise filtering by the probe designer. Biased pairwise analysis may also be utilized within intergenic regions, biasing towards to lesser-quality genes, mRNAs, transcripts, psuedogenes, est's, or exonic regions. In some embodiments, all of the intergenic regions of a chromosome may be pairwise filtered together, unlike the genes of a chromosome which are generally pairwise filtered separately.

Referring now to FIG. 6, is a flow chart of the events for one embodiment of the pairwise process for analyzing candidate probes for CGH arrays in accordance with the invention. At event 380, a probe set (e. g. a set of candidate probes within a gene or chromosome of interest) and a probe property are selected for pairwise analysis. An exemplary probe property is the duplex melting temperature of the candidate probes, designated as $T_i$ for each probe. Along with the probe property, an optimal parameter $T_o$ value (e.g. the average value of that property among all the candidate probes) is determined. At event 382, a single combined score value is generated that integrates the probe properties of interest weighted by their importance or utility in predicting good probe performance and all probes are marked as viable at event 384.

At event 390, the genomic distances $d_{ij}$ between neighboring viable candidate probes within the region of interest, (e.g.

on a specified chromosome, or gene of interest) is determined. "Genomic distance" means the number of nucleotide bases separating the two probe positions on the chromosome sequence of interest. The criteria for determining distances include but are not limited to; the distances between pairs of neighboring probes or the average distance of each probe from its two neighbors.

At event 400, the genomic distances between neighboring viable probes are determined, probes N with genomic distances less than a distance D are identified. The candidate probes are analyzed repeatedly for distance measurements until there are no remaining closely spaced probes i.e. $d_i$<D. Two neighboring probes spaced less than a distance D, are given preferential consideration over probe neighbors not meeting this criterion. Candidate probes are sorted from smallest distance between neighbors to largest genomic distance in the embodiment shown in FIG. 6, at event 400.

At event 410, candidate probes of the probe set are analyzed for duplex $T_m$ properties. The duplex $T_m$ is determined for each probe within a pair using established predictive formulas. In certain embodiments, the pair of probes may be analyzed for a plurality of properties other than Tm or in combination with Tm determination. In FIG. 6, the probes having a duplex $T_m$ value further from $T_o$ than that of their neighboring probe are flagged for elimination from the candidate probe set at event 420.

The process of analyzing a probe pair in event 410 and 420 is repeated a predetermined number of times as a matter of efficiency at event 430.

The duplex $T_m$ analysis is continued on the next probe pair at event 432. The next probe pair may be either; the next probe pair in order on the chromosome (region of interest), the next pair with the most closely space probes (e.g. comprise the smallest gap between probes), or the next two probes with the largest gap size. In the embodiment FIG. 6, the next neighboring pair to be analyzed for Tm values is the next pair with the largest distance.

At event 440, all of the probes flagged for elimination from the viable pool of probes in the region of interest are removed from the probe set. After one round of analysis based on the chosen probe property, i.e. $T_m$ in this example, event 390, 400, 410, 420, 430 and 440 are repeated in event 450 until all probes are have met the minimal distance criteria, or until the desired number of probes is achieved. In the subsequent rounds of pairwise analysis the probe neighbors change due to the elimination of some probes not meeting the distance criteria or the accepted values for the probe indicator selected, i.e. Tm. Exemplary probe indicators useful in pairwise analysis may include all of the probe selection criteria described above. In event 460, the remaining viable probes with appropriate distance parameters and the best values for the probe property or properties tested are selected.

Figure 7:
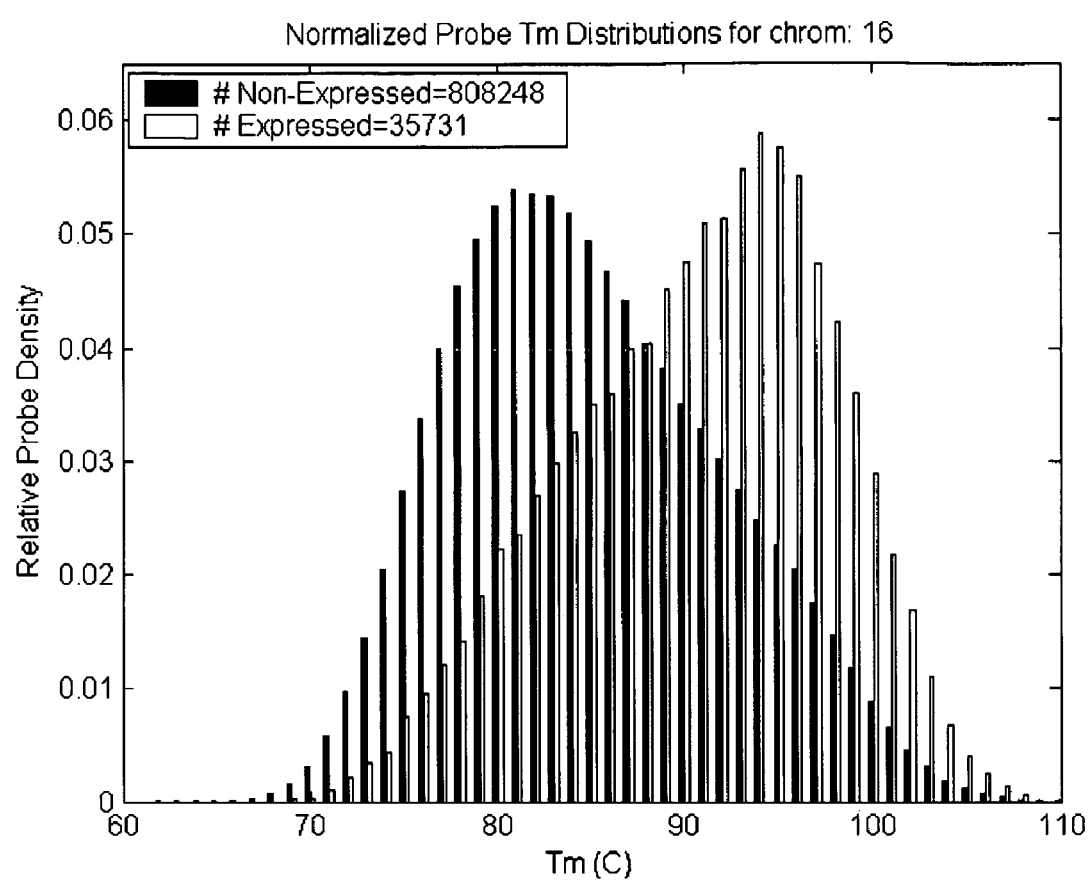
FIG. 7 is a histogram of all candidate probes for chromosome 16 to be subsequently analyzed using the pairwise probe filtering process in accordance with the invention.
Figure 8:
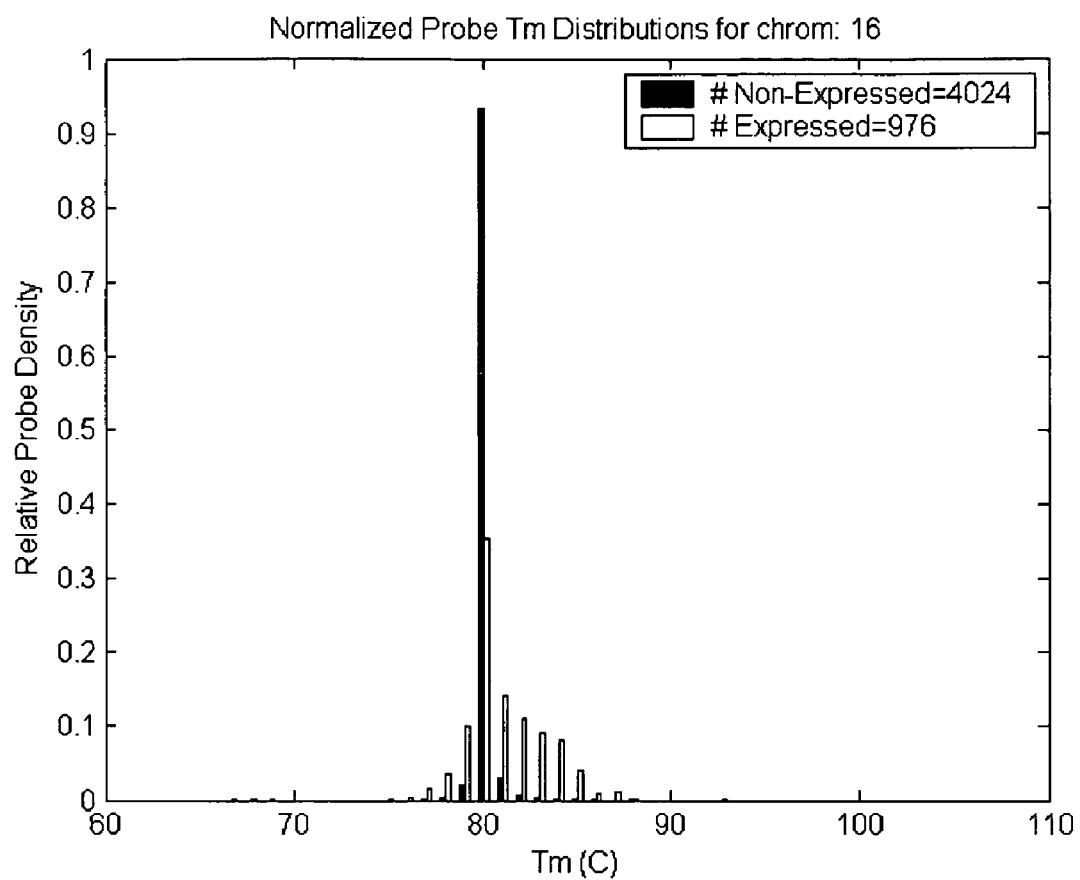
FIG. 8 is a histogram of filtered probe distributions demonstrating the probe filtering achieved by a pairwise analysis in accordance with the invention.

An example of the value of the pairwise analysis is shown in FIGS. 7 and 8. FIG. 7 is a graph of the $T_m$ distributions of all candidate probes for chromosome 16 prior to pairwise analysis. It should be noted that, due to the widely varying number of probes in the distributions, the vertical scales are given in terms of "Relative Probe Density," where the sum of all bars in each distribution is normalized to 1 in order to make the shapes of the distributions more apparent. The distribution for 60-mer candidate probes within intronic and intergenic regions is shown in white (808,285 probes) while the distribution of the candidate 60-mer probes within exon regions (about 4% of all) is shown in black (35,694 probes). The distributions of $T_m$s for all probes are fairly broad (about 20 degrees), and the average $T_m$'s differ between intronic and exonic probes by more than 15 degrees Celsius.

After applying a pairwise filtering which preferentially selected for probes with duplex $T_m$ values within a predetermined delta $T_m$ range, the probe set shown in FIG. 7 has be reduced in size considerably. The number of "surviving" candidate probes is reduced 170-fold from about 840,000 to 5,000 and the new distribution is shown in FIG. 8. This means that, on average, each probe remaining in the selected set was considered for elimination on at least seven occasions, and was kept each and every time. FIG. 8 is a graph showing the $T_m$ distributions of filtered probes for chromosome 16, where the filtering uses the pairwise probe selection algorithm, to reduce the number of probes while dramatically reducing the width of the $T_m$ distributions. The filtered distribution for probes within intronic and intergenic regions is shown with black bars (4,000 probes) while the distribution of the candidate probes within exon regions as indicated by white bars (976 probes). The filtered $T_m$ distributions shown in FIG. 8, with a full-width at half-maximum (FWHM) of less than 1 degree Celsius, are much narrower than their respective candidate probe distributions of FIG. 7. This pairwise analysis also demonstrates an enrichment of expressed sequences from about 4 percent of candidate probes to about 20 percent of filtered probes. It should be noted that while the pairwise algorithm is being used to select probes for CGH arrays, it may also be used for selecting probes of various array systems including but not limited to gene expression arrays. Some embodiments of the methods of the invention make use of an additional probe property to bias pairwise probe selection, for example in addition to the genomic distance and a probe property, such as duplex $T_m$.

Figure 9:
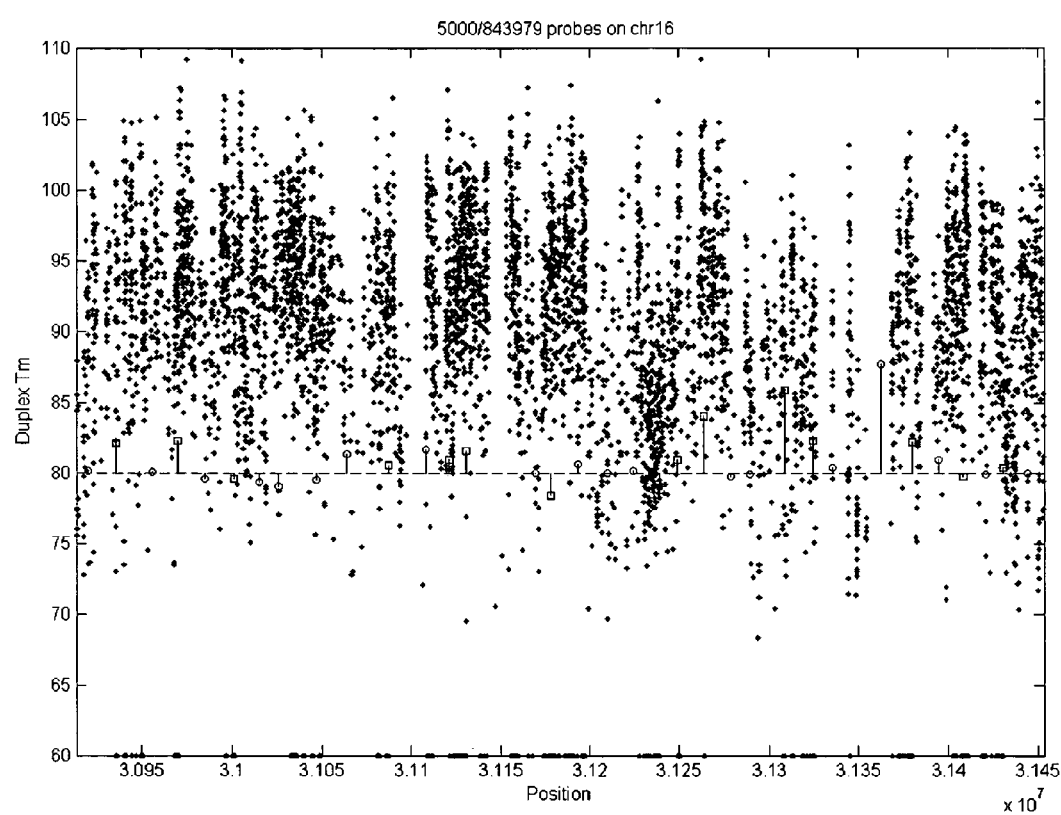
FIG. 9 is a graph of probes plotted along a small region of chromosome 16 where a subset of the probes plotted were selected by a biased pairwise analysis in accordance with the invention.

An example of the results of a pairwise analysis biased towards probes within an exon is shown in FIG. 9, as discussed above with regards to an example on chromosome 16. FIG. 9 shows a plot of the duplex melting temperatures of two sets of probes, in a narrow zoomed-in region (from 31 Mbp to 31.5 Mbp) plotted as a function of position along chromosome 16. The candidate probes are indicated as black dots, and the other selected probes comprising 5000 probes selected by the biased pairwise algorithm are indicated by the square and circular markers. The square markers in FIG. 9 correspond to selected expressed probes (probes for targets in exons), whereas the circular markers indicate probes selected in intragenic or intronic regions. Also shown along the bottom axis are points indicating the positions of probes that are within exon regions. The horizontal line at 80 degrees indicates the target temperature. Despite the reduction in mean temperatures from about 90 degrees (for expressed probes) to about 80 degrees, it can be seen that a substantial fraction of probes are selected within exons in this example and that many of the probes have temperatures quite near the target number of 80 degrees. Additionally, it can be seen that the selected probes are reasonably uniformly spaced.

It should also be noted that while the pairwise and biased pairwise filtering processes are being used to select probes for CGH arrays in the embodiment described above, they are also useful for selecting probes of various array systems including but not limited to location analysis, expression arrays, and the like.

Figure 10:
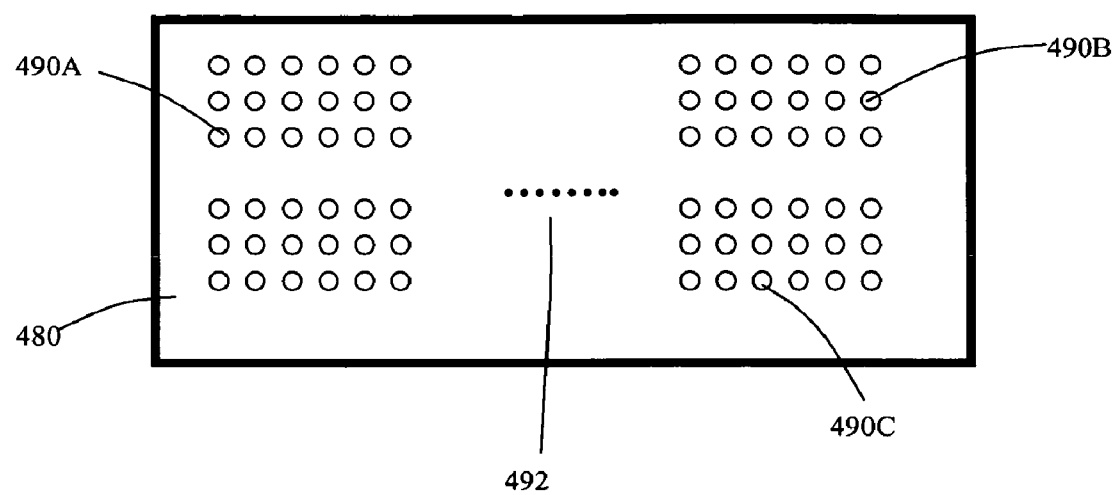
FIG. 10 is a block diagram of a microarray comprising probes with selected duplex Tm properties in accordance of the invention.

The of probes utilized for the microarrays of the instant invention were selected by the methods described above. The microarrays of the invention comprise a solid support in which a plurality of the selected polynucleotide probes are bound to the surface, or attached to the solid support of the array. Techniques known to those skilled in the art of microarray manufacturing are utilized in attaching the probes to the solid support. The plurality of polynucleotide probes attached to the support have a corresponding plurality of different nucleotide sequences. FIG. 10 is a block diagram of a microarray comprising a solid support 480 and a plurality of nucleotide probes, 490A, 490B and 490C attached to the solid support. 490A, 490B and 490C are only representative of the probes on the array and the dots, 492, on FIG. 10 indicate that at least 1,000 probes may be placed on the solid support. The number of probes placed on the array may range from about 1,000 to about 50,000, more particularly from about 10,000 to about 40,000 depending on the intended use of the microarray. In certain embodiments the number of probes on the array may be about 1,000, 2,000, 5,000, 10,000, 20,000, 30,000 or about 40,000. The nucleotide probes on the microarrays of the invention were selected for specific probe properties determined by the methods of the invention.

The probes of the microarray comprise similar thermodynamic properties identified by the methods of the invention. A large percentage of the probes bound to the solid support comprise a duplex Tm value which falls within a very narrow Tm distribution or delta Tm of about 0.25° C. to about 5° C., usually about 0.25° C. to about 3° C., more usually 0.25° C. to about 2° C. Delta Tm is defined as a temperature distribution in which Tm median is approximately in the center of the distribution. Probes which are within the delta Tm may have a duplex Tm greater than the median Tm−(delta Tm)/2 but less than median Tm+(delta Tm)/2. Most of the melting temperatures spanned by the delta Tm usually fall within the temperature range of about 65° C. to about 90° C. when calculated by the method described in J Breslauer et al. Proc Natl Acad Sci. (PNAS) 1986 June; 83(11): 3746-3750, where the target and probe concentrations are both 0.1 pM and the salt concentration term is set equal to zero. Thus, consideration must be given to the experimental conditions in which duplex Tm values have been calculated.

A microarray having probes which have very similar Tm values, has been shown experimentally, to be very effective in CGH and location analysis.

The percent of probes which have a duplex Tm value within a delta Tm of about 5° C. degrees is from about 60% to about 99%, usually about 80% to about 99%, and more usually about 95% to about 99%. The percent of probes which have a duplex Tm value within a delta Tm of about 4° C. degrees is from about 50% to about 99%, usually about 80% to about 99%, and more usually about 90% to about 99%. The percent of probes which have a duplex Tm value within a delta Tm of about 3° C. degrees is from about 50% to about 99%, usually about 80% to about 99%, and more usually about 90% to about 99%. The percent of probes which have a duplex Tm value within a delta Tm of about 2° C. degrees is from about 50% to about 99%, usually about 80% to about 99%, and more usually about 90% to about 95%. The percent of probes which have a duplex Tm value within a delta Tm of about 1.5° C. degrees is from about 50% to about 99%, usually about 70% to about 95%, and more usually about 80% to about 90%. The percent of probes which have a duplex Tm value within a delta Tm of about 1.0° C. degrees is from about 50% to about 99%, usually about 70% to about 95%, and more usually about 70% to about 85%. The percent of probes which have a duplex Tm value within a delta Tm of about 0.5° C. degrees is from about 50% to about 99%, usually about 50% to about 90%, and more usually about 50% to about 80%.

The majority of probes attached to the solid support have a duplex Tm value ranging from about 65° C. to about 85° C., usually from about 75° C. to about 85° C., more usually from about 78° C. to about 82° C. Tm values for a particular probe may varying due to the salt concentration in the probe solution, target concentration, probe concentration as well as other factors. In one embodiment, the percent of probes on the solid support which have a duplex Tm value between 65° C. to about 85° C. is about 90% to about 100%. In another embodiment, the percent of probes on the solid support which have a duplex Tm value between 75° C. to about 85° C. is about 90% to about 99%. In yet another embodiment, the percent of probes on the solid support which have a duplex Tm value between 77° C. to about 82° C. is about 85% to about 99%. Other embodiments may have a percent of the probes having a duplex Tm value between 79° C. to about 81° C. from about 85% to about 98%.

Table 1 gives the Tm values and Tm distributions for probes for one embodiment of a microarray of the invention. In this embodiment, microarray HGA1.1, has approximately 40,000 unique probes which have very similar Tm values. Table 1 shows that the majority of the probes (92%) of the HGA1.1 have a Tm value between 79° C. and 81° C. During the probe selection process for the HGA1.1 array, the Tm distribution for the probes was set narrowly around a median Tm of 80° C. which filtered out a larger number of candidate probes which did not fall within the specified Tm range. Table one also demonstrates the use of a duplex Tm cutoff temperature, in this embodiment, candidate probes with a Tm greater than 81° C. were not selected.

Figure 11:
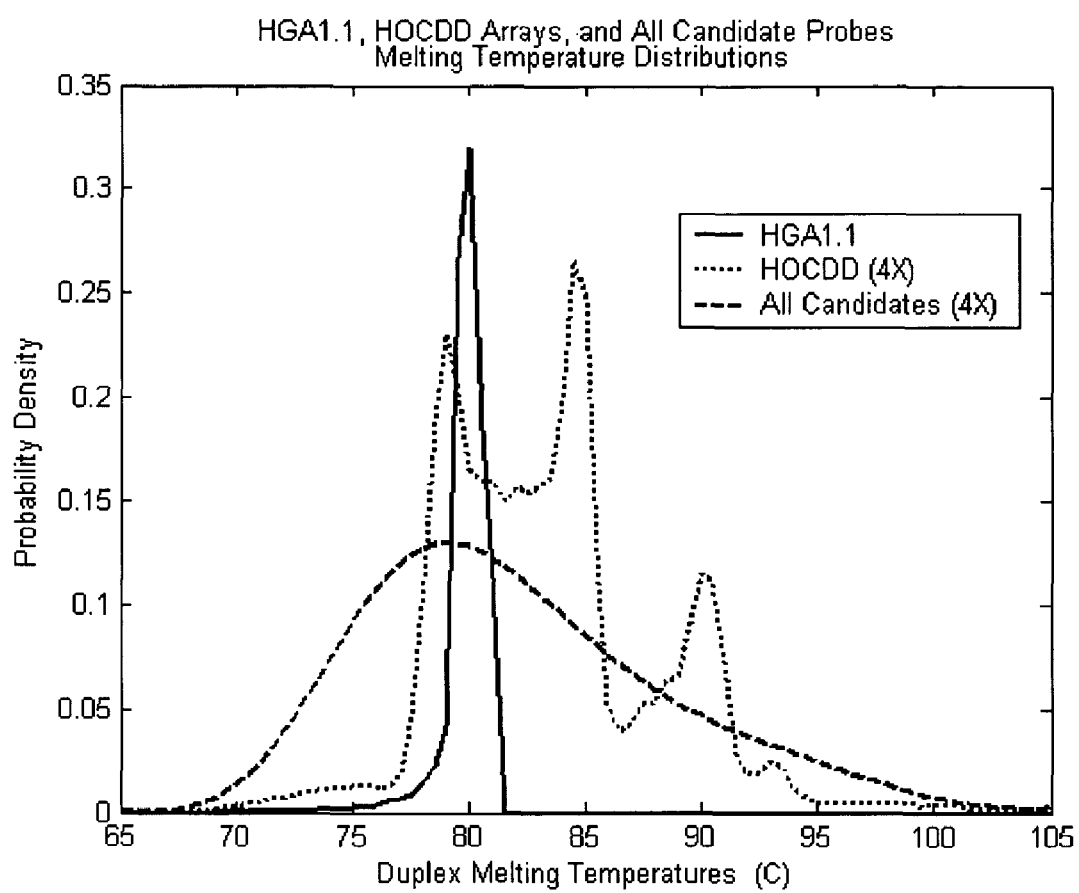
FIG. 11 is a graph of the duplex melting temperatures of probes of an expression array compared to the duplex melting temperatures of probes on a microarray in accordance of the present invention.
Figure 12:
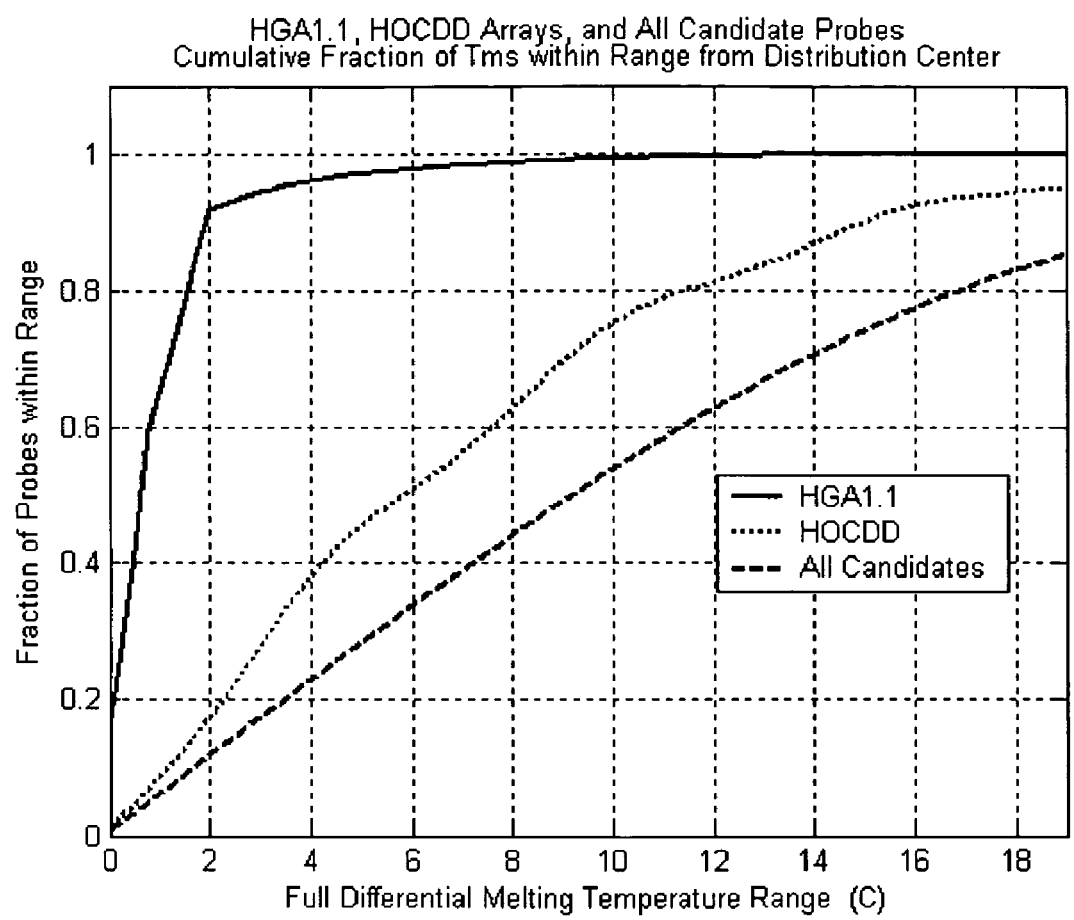
FIG. 12 is a graph of the fraction of probes within a differential duplex melting temperature range for probes on a gene expression array compared to probes on a microarray in accordance with the invention.

Referring now to FIG. 11, is a graph comparing the $T_m$ distributions of probes of a microarray in accordance with the invention, to the candidate probes utilized to make the microarray as well as probes from a typical expression array. The HGA1.1 array, as described above, is one embodiment of the invention and is represented as solid line in FIG. 11, while HOCDD, an expression array is shown as a dotted line and the candidate probes, prior to $T_m$ selection are shown as a dashed line. Both arrays comprise approximately 30,000 to 40,000 probes of 60 bases in length, while approximately 30 million non repetitive candidate probes prior to filtering are also shown in FIG. 11. FIG. 11 shows that the selected probes utilized in fabricating the microarrays of the invention, in general, have a very narrow $T_m$ range in comparison to the expression array or the initial candidate probes. The $T_m$ median for the exemplary microarray, HGA1.1, shown on FIG. 11 is about 80° C., which corresponds to 36% GC content, using the Tm calculation utilized by the inventors. The fraction of probes within a differential or delta Tm range for the two arrays as well as all the candidate probes is shown in the graph of FIG. 12. FIG. 12 emphasizes the large number of probes utilized for the microarrays of the invention with similar $T_m$ values. Over 90% of the probes of HGA1.1 are within a 2 degree $T_m$ differential, while less than 20% of the probes of the HOCDD expression are within a 2 degree $T_m$ differential. Both FIGS. 11 and 12, demonstrate one of the novel features of certain embodiments of the microarrays of the invention.

TABLE 1

Tm values of probes on HGA1.1 microarray.

| Tm Range | Tm Distribution of probes |
|---|---|
| 65 | 0 |
| 65.5 | 0 |
| 66 | 0 |
| 66.5 | 0 |
| 67 | 0 |
| 67.5 | 0 |
| 68 | 0 |
| 68.5 | 0 |
| 69 | 1 |
| 69.5 | 3 |
| 70 | 2 |

TABLE 1-continued

Tm values of probes on HGA1.1 microarray.

| Tm Range | Tm Distribution of probes |
|---|---|
| 70.5 | 5 |
| 71 | 8 |
| 71.5 | 13 |
| 72 | 20 |
| 72.5 | 24 |
| 73 | 29 |
| 73.5 | 51 |
| 74 | 53 |
| 74.5 | 63 |
| 75 | 97 |
| 75.5 | 114 |
| 76 | 153 |
| 76.5 | 212 |
| 77 | 262 |
| 77.5 | 360 |
| 78 | 586 |
| 78.5 | 904 |
| 79 | 1668 |
| 79.5 | 10658 |
| 80 | 12769 |
| 80.5 | 7385 |
| 81 | 4535 |
| 81.5 | 0 |
| 82 | 0 |
| 82.5 | 0 |
| 83 | 0 |
| 83.5 | 0 |
| 84 | 0 |
| 84.5 | 0 |
| 85 | 0 |

In certain embodiments, probes attached to a support have a nucleotide length ranging from about 20 nucleotides to about 100 nucleotides, usually about 40 nucleotides to 70 nucleotides, and more usually about 50 to 65 nucleotides in length. In some embodiments all the probes on the array have the same length, for example a length of about 60 nucleotides. In other embodiments the about 40% to about 60% of all the probes have a length of 60 nucleotides. During the probe selection process described in the methods of the invention, some of the probes are trimmed or shortened to change the $T_m$ of the probe so that it falls within a predetermined delta $T_m$ range. Thus some of the probes on the array may be shorter than others.

In certain embodiments, the probes of the microarray comprise similar GC content identified by the methods of the invention. A large percentage of the probes bound to the solid support comprise a % of GC content which falls within a very narrow % GC distribution or delta % GC of less than about 10%, usually about 5%, and more usually 3%. Delta % GC is defined as a distribution of % GC content of probes, in which the % GC content median is approximately in the center of the distribution. Probes which are within the delta % GC may have a GC content greater than the median % GC−(delta % GC)/2 but less than median % GC+(delta % GC)/2. The delta % GC usually falls within the GC content range of about 30% GC content to about 50% GC content for a given probe. A microarray having probes which have very similar % GC content, has been shown experimentally, to be very effective in CGH and location analysis.

The percent of probes which have a % GC content within a delta % GC of less than 10 is from about 60% to about 99%, usually about 70% to about 90%, and more usually about 80% to about 90%. The percent of probes which have a % GC content within a delta % GC of less than 5 is from about 40% to about 90%, usually about 60% to about 90%, and more usually about 70% to about 90%. The percent of probes which have a % GC content within a delta % GC of less than 3 is from about 35% to about 80%, usually about 40% to about 70%, and more usually about 40% to about 65%.

In one embodiment, about 60% to about 99% of the polynucleotide probes attached to the solid support have a % GC content from the range of 30% to 40%. In another embodiment, about 60% to about 95% of the polynucleotide probes attached to the solid support have a % GC content from the range of 34% to 40%. In yet another embodiment, about 70% to about 90% of the polynucleotide probes attached to the solid support have a % GC content from the range of 34% to 40%.

Figure 13:
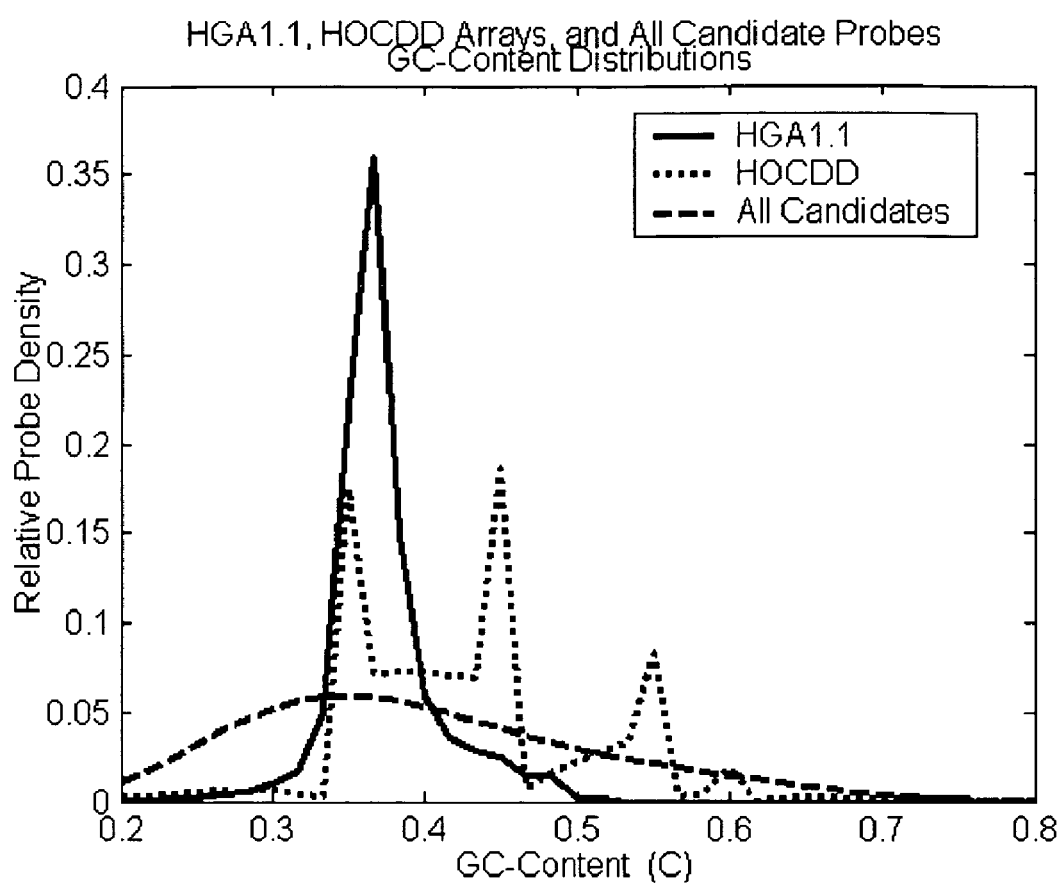
FIG. 13 is a graph of the % GC content of probes of an expression array, compared to the % GC content of probes on a microarray in accordance of the present invention.

FIG. 13 Referring now to FIG. 13, is a graph comparing the GC content distributions of probes of a microarray in accordance with the invention, to the candidate probes utilized to make the microarray as well as probes from a typical expression array. The HGA1.1 array, as described above, is one embodiment of the invention and is represented as solid line in FIG. 13, while HOCDD, an expression array is shown as a dotted line and the candidate probes, prior to GC content selection are shown as a dashed line. Both arrays comprise approximately 30,000 to 40,000 probes of 60 bases in length, while approximately 30 million non repetitive candidate probes prior to filtering are also shown in FIG. 13. FIG. 13 shows that the selected probes utilized in fabricating the microarrays of the invention, in general, have a very narrow delta or differential % GC content range in comparison to the expression array or the initial candidate probes. The fraction of probes within a differential or delta % GC content range for the two arrays as well as all the candidate probes is shown in the graph of FIG. 14.

Figure 14:
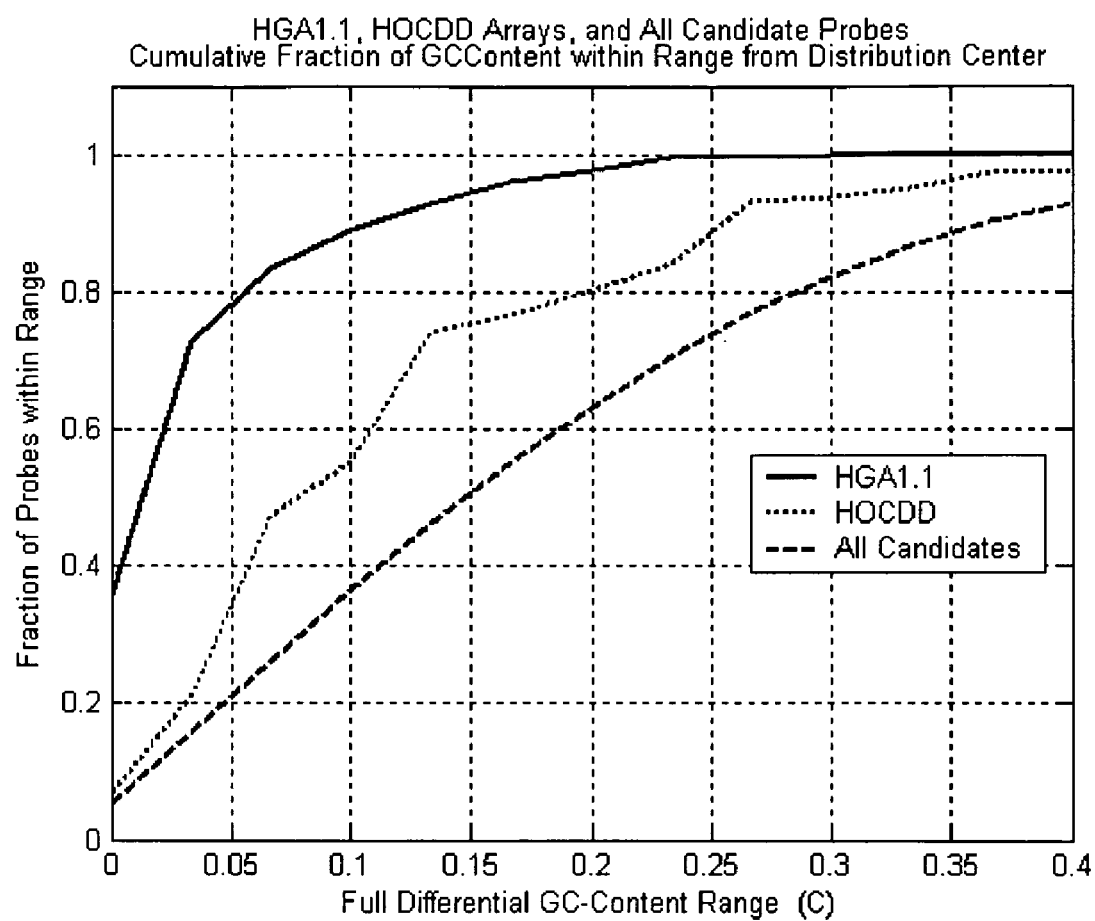
FIG. 14 is a graph of the fraction of probes within a differential/delta % GC content for probes on a gene expression array compared to probes on a microarray in accordance with the invention.

FIG. 14 emphasizes the large number of probes utilized for the microarrays of the invention with similar % GC content values. Approximately 80% of the probes of HGA1.1 are within a 5% GC content differential, while less than 40% of the probes of the HOCDD expression array are within a 5% GC content differential.

In some embodiments the probes on the array target various regions of the human genome such as exons, introns, regulatory regions and intergenic regions. In other embodiments the probes target a different genome than human, such as mouse, rat, etc. In one embodiment, at least 30% of the probes which target exons. In another embodiment, at least 5% of the probes of the microarray target regulatory regions. In yet another embodiment, at least 50% of the probes on the support target intergenic regions.

While the microarrays of the invention are useful for CGH and location analysis they are not limited to these types of analysis. For example, the microarrays of the invention may be utilized expression analysis as well.

Figure 15:
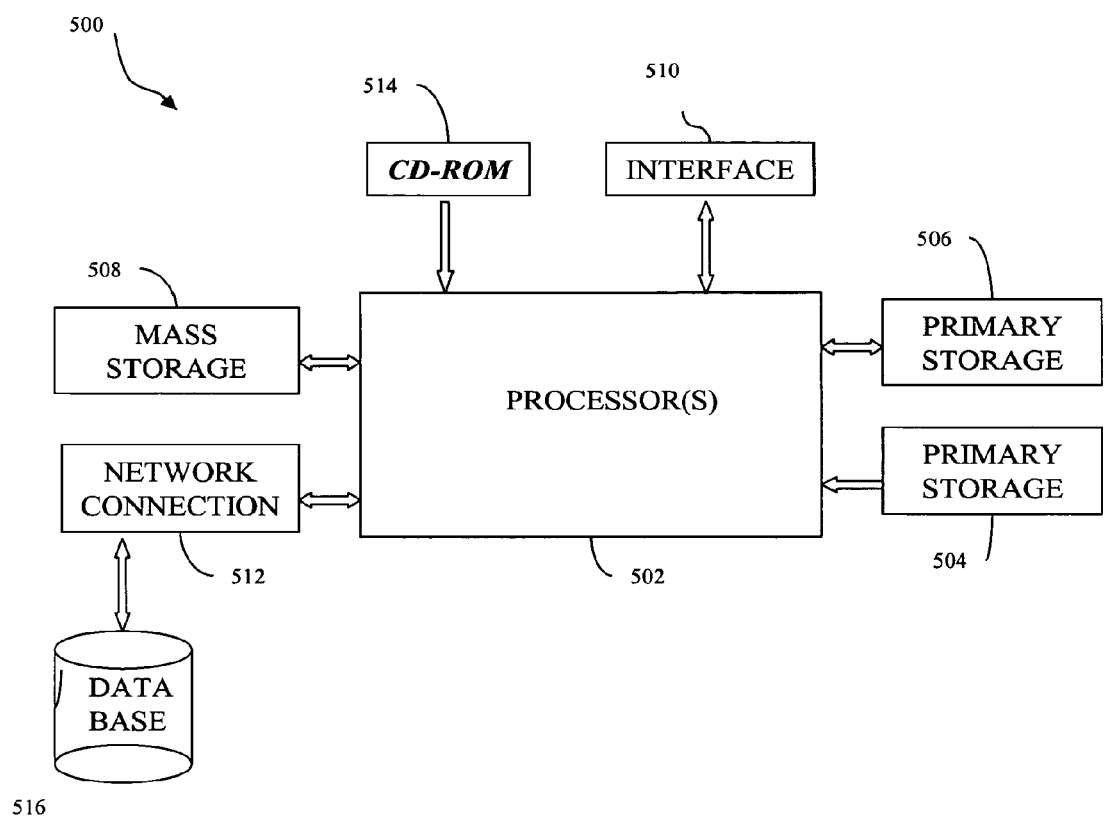
FIG. 15 is a block diagram illustrating an example of a generic computer system which may be used in implementing the present invention.

FIG. 15 illustrates a typical computer system 500 that may be used in processing events described herein. The computer system 500 includes any number of processors 502 (also referred to as central processing units, or CPUs) that are coupled to storage devices including primary storage 506 (typically a random access memory, or RAM), primary storage 504 (typically a read only memory, or ROM). As is well known in the art, primary storage 504 acts to transfer data and instructions uni-directionally to the CPU and primary storage 506 is used typically to transfer data and instructions in a bi-directional manner Both of these primary storage devices may include any suitable computer-readable media such as those described above. A mass storage device 508 is also coupled bi-directionally to CPU 502 and provides additional data storage capacity and may include any of the computer-readable media described above. Mass storage device 508 may be used to store programs, data and the like and is typically a secondary storage medium such as a hard disk that is slower than primary storage. It will be appreciated that the information retained within the mass storage device 508, may, in appropriate cases, be incorporated in standard fashion as part of primary storage 506 as virtual memory. A specific mass storage device such as a CD-ROM 514 may also pass data uni-directionally to the CPU.

CPU 502 is also coupled to an interface 510 that includes one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. The CPU 502 optionally may be coupled to a computer or telecommunications network using a network connection as shown generally at 512. With such a network connection, it is contemplated that the CPU might receive information from the network, or might output information to the network in the course of performing the above-described method steps. Finally, a data base 516 is bi-directionally coupled to network connection 512 for data storage and retrieval for information pertaining to the probe design process and microarray fabrication. The above-described devices and materials will be familiar to those of skill in the computer hardware and software arts.

The hardware elements described above may implement the instructions of multiple software modules for performing the operations of this invention. For example, instructions for population of stencils may be stored on mass storage device 508 or 514 and executed on CPU 508 in conjunction with primary memory 506.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example I

This example utilized a single array design, with 22000 features, and included candidate probes for five chromosomes: Chr16, Chr17, Chr18, ChrX and ChrY. The test array had approximately three times as many probes, for each chromosome, as were eventually needed. The purpose of the test experiments was to select the best probe, according to the criteria described above, from these 3-fold redundant probe candidates.

The probes were designed and selected for five chromosomes, Chr16, Chr17, Chr18, ChrX and ChrY. Each chromosome was analyzed separately as a genomic range of interest, and probes for that chromosome which met the in-silico probe criteria (event 40 of FIG. 1) were placed onto a semi-final array. Below are the events which were carried out to identify candidate probes to be placed on a semi-final array.

Restriction digest of genomic sequences: Each chromosome was subjected to a computational process that models the restriction digest of the hybridization assay by cutting the chromosomal DNA sequences in silico at the sites which would be cut in the experimental assay. In this example we used the restriction enzymes, Rsa1, which cuts at the "|" in GT|AC and Alu1, which cuts at AG|CT. Each cut site is identified in the sequence, allowing these sites to be omitted from potential probe sequences, thus decrease the computational time needed to analyze the probes.

Target Fragment filtering: Here potential target sequences were filtered by size, number of repeat-masked bases and/or GC-content. Target fragments shorter than a nominal probe length, i.e. <60 bp were eliminated. Fragments with a length greater than 800 bp were also removed from the target fragment set. The latter cutoff was determined by a visual inspection of the longer target sequences for repetitions. Many, if not most sequences >800 bp have a relatively low sequence complexity that is often obvious on visual inspection. Target fragments that were largely repeat masked were also removed from the target fragment set.

Candidate Probe Tiling: Possible probes were then tiled across non-repeat-masked regions. 60-mer candidate probes were tiled in steps of 30 bases. Although these candidate probes are generated as 60-mers, some of these probes were subsequently shortened to anywhere from 30 to 59 bases in latter steps. The probe tiling procedure initiates a new probe at the first non repeat-masked base within a target sequence, if a repeat-masked section is encountered, the tiling procedure is restarted at the next first non-repeat masked base. The tiling process was carried out for each chromosome of interest and allowed for the generation of candidate probes for each of the five chromosomes.

Thermodynamic Annotation of Candidate Probes: After the generation of candidate probes, probes were annotated with their estimated duplex $T_m$, the melting temperature of a probe forming a duplex with its perfect-match target sequence, in silico. This quantity is useful as an indication of the GC-content of the probe and a measure of the duplex stability.

Annotation of probes for expression and association with genes: After annotating the candidate probes by duplex $T_m$, a number of databases were used to determine probe sequences which are contained within introns or exons of either known genes or predicted genes. Message alignments to genomic sequences were identified, and probes were analyzed for whether they were either partially or wholly contained within the confines of the exons of the messages. Probes were annotated independently for whether they are in intron regions or within the bounds of a message or within a "premRNA".

Exonic Probe Sets: The candidate probes were then filtered for expression and duplex $T_m$. Under our experimental conditions, higher duplex $T_m$ probes were found to behave quite poorly relative to lower $T_m$ probes. Very low $T_m$ probes form unstable duplexes and hence have much lower signals. As a result, those probes with duplex $T_m$'s below about 65 degrees and above 90 degrees were filtered out. The median $T_m$ for all probes was between 79 and 80 degrees. After the $T_m$ filtering, candidate probes which center or middle nucleotide bases lie within the limits of any exon of known and predicted genes and mRNAs were considered.

A homology search was completed for the remaining filtered candidate probes in expressed regions, thus producing an exonic ProbeSet. These homology search results were integrated with other probe parameters and for annotation of the exonic ProbeSet.

Intronic Probe Sets: Candidate probes which were in introns of known genes, (intronic ProbeSet) mRNAs and predicted genes were selected but at a somewhat reduced density then was used for the exonic ProbeSet. This step involves the use of the pairwise selection algorithm, which analyzes neighboring probes, and selects/scores one probe over the other by analyzing the neighboring probes for a certain probe parameter.

The size of the intronic Probe set was chosen so the homology search can run in about 2-days per chromosome on a single CPU. A homology search was run in the expressed regions for the intronic ProbeSet. The homology search results were integrated with other probe parameters for annotation of the intronic ProbeSet by those parameters.

Uniformly-spaced Probe Set: Another probe set was produced in which the number of probes is reduced from the broad candidate set, by eliminating probes within known genes and thinning to create a fairly low-density probe set that covers the whole genome. This probe set was chosen to be of such a size that each chromosome could be homology searched in less than 2 CPU days. After pairwise filtering to remove closely spaced candidate, a homology search was conducted and the search results were integrated with other probe parameters for annotation of the intergenic Probe Set.

Gene by Gene Probe selection: The final probe set for the whole human genome array will comprise a plurality of probes for each known human gene. To accomplish this, the following events were carried out. The homology searched exonic, intronic and intergenic probe sets were combined, and these presets were filtered for homology, keeping only those probes which were 60-mers. The 60-mer probes were annotated for membership in either of two public transcript databases: knownGene and RefSeq. The messages (i.e. transcript sequences) were analyzed, and for each message a set of candidate probes were selected. If the message was spanned more larger distances on the genome (say more than 200,000 bp), then about 6 or 7 candidate probes were selected. For shorter messages, the candidate probe set only contained 3 to 5 probes. If there were more probes within the boundaries of the gene (or message), than the target numbers from 4 to 7, the probes were thinned to the desired number by using the biased pairwise probe filtering selection within the genomic boundaries (as described above) in a gene-by-gene fashion. These numbers were used to create a 6-array set of single density arrays (about 20,000 probes per array). These were subsequently pared down (using indirect validation methods) to 40,000 probes for a double-density array, reducing the number of probes to one per gene and three per gene believed to be associated with cancer genomics. The remaining real estate on the array was filled with appropriately pairwise filtered probes from the uniformly-spaced intergenic probe set discussed above.

In this design process, the bias was towards exonic regions over intronic, with a $T_m$ bias of 5 degrees from the desired optimum $T_m$. If the duplex $T_m$ of the exonic probe was more than 5° C. further from the optimum $T_m$ than that of its intronic neighbor, the intronic probe was selected, otherwise the probe within the exon was chosen. Across the genome this bias increased the likelihood of picking probes within exons from about 3% to about 50%.

In general, if the desired number of candidate probes were equal to the number of filtered probes in the given region, then they were simply selected. If there was a lesser number in the gene region, then the region-of-interest was expanded into flanking regions in steps of 2,000 bp, until the desired number of candidate probes was reached, or until a maximum distance of 20 kB by was analyzed, and at which point, the gene was flagged as "missing". A more exhaustive search for probes was subsequently carried out for missing genes as described below.

There are two main reasons that good probes may not be found within a given gene, message, or region. The first is that the region may be exceptionally GC rich or high in duplex melting temperature (and in secondary structure). For example, it has been determined that expressed regions, such as introns have substantially higher melting temperatures than unexpressed regions. The second reason that good probes may not be found within a given gene, message, or region is that the region may be highly homologous to one or more other regions of the genome. A good example of this is the pseudo-autosomal regions of the X and Y chromosomes. These regions from 0 to 2.5 Mbp and from 87 to 91 Mbp on chrX are duplicated on chrY. Probes selected in this gene-by-gene process were joined into a new table of "semi-final probes" for placing on an array for further validation and testing.

Iteration for Missing Genes: For those genes or messages flagged as "missing" in the previous step, the homology search was intensified/expanded to help identify these genes. The original unfiltered candidate probe set generated above, was revisited. For each of the genes or messages missed in the first round, 400 new candidate probes were selected, upon which to perform a new homology search. These candidate probes were chosen, first within the gene (or message) region of interest, and then in flanking regions of the gene in steps of several thousand base pairs. Then a homology search was carried out on the newly identified probes. The homology search results were joined with other probe set annotation, and then these probe sets were combined with the exonic, intronic and intergenic probe sets.

The stringency of the homology filter was reduced to HomLogS2B for those probes with a homology score of less than 10 (e.g. an equivalent distance of 10 bp). The amount to reduce the homology filter was determined from obtaining good validation results for probes with homology scores in the range of 10-20. Probes were searched as stated above, but this time the search was expanded to a maximum limit of 400,000 bp beyond the limit of the gene of interest.

"Wasteland" probes: The selection of probes at a more reduced density between known and predicted genes, the intergenic ProbeSet, is sometimes called the "wasteland" probe set. Genes are not uniformly spaced across the genome or within any given chromosome, consequently, despite a major interest in selected probes for genes, or gene-regions, it is valuable to have some low-density probe coverage for the intergenic regions. These intergenic regions may be of interest either because of their regulatory value or for purely exploratory research purposes. For this reason, a number of candidate probes (300-800/chromosome) were reserved for intergenic regions of each chromosome, depending of the length of the chromosome. These regions include but are not limited to predicted genes as well as mRNA not yet associated with known genes. Of course, arrays for location analysis are specifically designed to focus on intergenic regions, especially those regions just upstream of a genes 5'-end.

The process for selecting wasteland probes is described below. The uniformly-spaced probe set produced above is filtered for probes with a HomLogS2B score greater than 19. Any previous expression annotation is cleared and the filtered probe set is "reannotated" for membership in either of the two public transcript databases, knownGene and/or RefSeq. If the probes are within these known genes, they are removed from the wasteland ProbeSet. The remaining probes are than analyzed and annotated for mRNAs and predicted genes.

The probe set is then thinned to approximately 300 to 800 probes from about 130,000 filtered probes initially using the biased pairwise analysis. The biased pairwise analysis was based on the length of the chromosome, while biasing probe selection toward a central $T_m$ of 80 degrees as well as towards expression (e.g. biased toward mRNAs and predicted genes) with an additive bias of 5 degrees Celsius.

Probes for pseudo-autosomal regions of Chromosomes X and Y: It is well known among genomic biologists that there are regions on chromosome-Y that are virtually identical to chromosome X. These regions are called pseudo-autosomal despite the fact that they exist on very different chromosomes, because they contain the same genes, and these genes nominally manifest themselves in two copies per cell, independent of sex. For this reason, these regions were represented on a prototype array. Pseudo-autosomal regions are found mainly in two places in the human genome; the first place is about 2.5 megabases of both ChrX and ChrY, and the second is from 87-91 Mbp on chrX. 300 probes were selected to span this region more or less uniformly and biased towards expression with the pairwise algorithm. Out of the 300 probes, 53 probes were selected within exons, and 215 in introns.

Finalizing the probe data set: The probe data set was finalized by collecting all of the identified probes sets mentioned above and evaluated as follows. Firstly, the gene-by-gene probe set, the missing gene probe-set, and the wasteland probe-set described for all chromosomes were combined into a single table. The prior expression annotation was reset (cleared) and the probes were reannotated with gene names in reverse or of database validation, predicted first, mRNAs, MGCgenes, knownGene, and RefSeq. The genes on the forward strand as well as the reverse strand are kept for each probe.

For probes that are within exons on the reverse strand but not within exons on the forward strand, the complement of the reverse strand sequence was taken. This allows one array to be used for both gene-expression as well as for CGH. The probes within a message may still be viable for expression arrays, although their distances from the 3' ends of the message will vary.

60-mer probes were trimmed or shortened in length as necessary to achieve a $T_m$ below 81 degrees. Probe performance for 60-mer probes is dramatically better for probes with low $T_m$ (below about 80 degrees) than probes with a higher $T_m$. It has been demonstrated empirically that the performance of high $T_m$ 60-mer probes can be improved somewhat by shortening them.

The trimming process for each high $T_m$ 60-mer probe (typically chosen in an expressed region) involves searching each probe sequence for the longest sequential subsequence with a melting temperature less than a cutoff, typically 81 degrees, and utilizing that subsequence instead of the full length 60-mer sequence.

Array Layout: Finally, the selected probes for each chromosome were placed on an array. This was completed by exporting the selected probes to a text file in table form in a 4-field format and loaded into the Agilent's Array Wizard internal software for generating the new array design.

Example II

In this example, validation experiments were completed using male and female samples, and cell lines containing non-naturally occurring copy numbers of X, such as 3X, 4X and 5X. The experiments were conducted using an array specifically designed for CGH, designated D4CGH1, which included over 2000 probes designed specifically for chromosome X. These candidate probes were made in three lengths 60-mers, 45-mers and 30-mers. Male and female samples were hybridized on these arrays in replicate experiments. From these data, the slope (i.e. the separation between the distributions of X-chromosome probes, which have a nominal log 2 ratio of −1 for male vs. female samples, and the autosomal probes, which have a nominal log 2 ratio of 0), and noise measurements (i.e. the widths of the distributions of X-chromosome probes and of autosomal probes) were calculated, and subsequently, rules for determining the viability of probes in silico were established by this experiment as well as others.

Probes that were determined by the homology search to be less than ideal were intentionally placed on the array as controls. Also included on the array were probes having various duplex Tm's and hairpin stabilities, to provide a broad range of duplex melting temperatures and hairpin stabilities. As a result, duplex Tm's and hairpin stabilities could be empirically determined, and these two probe properties could be used as metrics for predicting the performance of our probes in future array designs.

Figure 16:
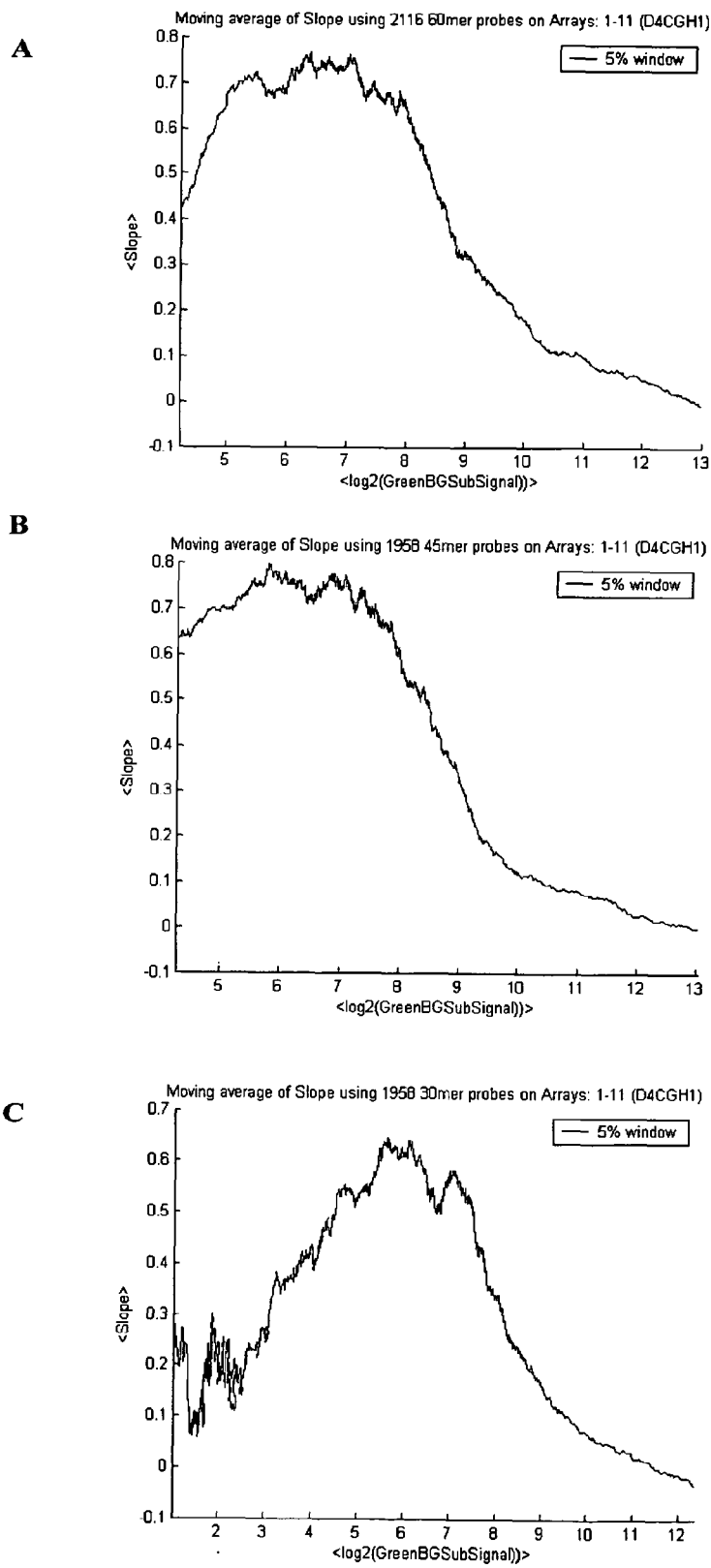
FIGS. 16a, b, c are histograms showing the relative signal strength of candidate probes of various lengths in accordance with the invention.
Figure 17:
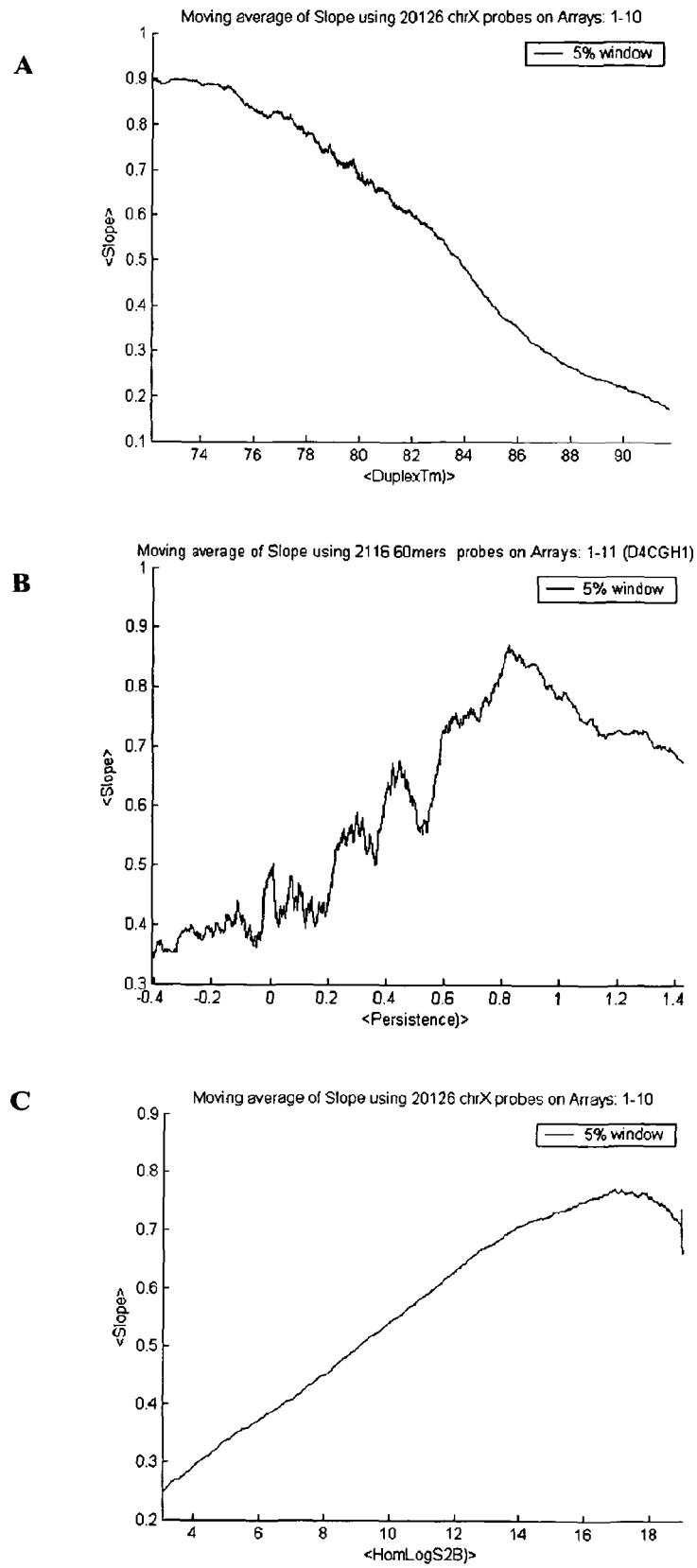
FIG. 17a is histogram showing the responsiveness of candidate probes to duplex Tm in accordance with the invention.
FIG. 17b is histogram showing the responsiveness of candidate probes to binding persistence analysis in accordance with the invention.
FIG. 17c is a histogram showing the responsiveness of candidate probes to HomoLogS2B analysis in accordance with the invention.

To see the effectiveness of several other probe properties, we plotted smoothed curves representing the slopes and p-values of the probes as a function of various parameters as shown in FIGS. 16 and 17.

Here, the metric utilized and determined on a probe-by-probe basis is the slope (which is a measure of the response of the Log Ratio to chrX genomic copy number for the target) of each probe. It is expected that for good probes higher slopes will be obtained (ideally approaching 1.0) and conversely lower slopes indicate poor performing probes. In FIG. 16a, each point on the curve represents the mean of a narrow band (5%) of probes, calculated as a moving average over the full range of the parameter under test. The y-axis represents the moving average of the slopes (calculated as the log-ratio of dye-normalized signals of the male sample to the female sample), whereas the X-axis points represent the moving average of the log (in base2) of the back-ground subtracted signals for the probes in the reference channel, where the reference sample was a normal female sample with two copies of the X-chromosome in each cell. For the background subtracted signal of the reference channel, we can see that the slopes are fairly high for most of the lower half of the range and drops precipitously above a log 2 value of 8, which is about 250 counts. The slopes are also decreased at the bottom of the signal distribution, probably as a result of the greater relative noise near the detection limit of the system. The reason for the poor response of the probes at the higher end of the signal range is likely related to the specificity of the probes. Even though these probes may have good homology scores, many of these poor performing high-signal probes are probably binding non-specifically to unintended targets. Results are shown for 60-mers in FIG. 16a, similarly for 45-mers in FIG. 16b, and for 30-mers in FIG. 16c. Results are quite similar for the 45-mers and 60-mers with maximal slopes approaching 0.8, and substantially worse for 30-mers, which simply appear to have insufficiently duplex stability under these hybridization conditions.

Equivalent curves are shown (without p-values) in FIGS. 17a, b, and c for other metrics and probe properties. FIG. 17a shows the relationship between the performance of probes and their duplex $T_m$'s. The plot shows a relatively better probe response for lower duplex $T_m$ and poor response for probes with higher melting temperatures. Although there is improved probe performance below the temperature of 78 degrees, there are relatively low probe densities at these lower temperatures and a maximum of available probes at about 80 degrees. These curves are clearly are dependent of the experimental conditions as well. The operating point of 80 degrees represents a trade off between probe performance and the density of available probes. The maximum slope of about 0.9 at the low end of the distributions indicates that melting temperature is probably a very effective in silico metric. FIG. 17b, shows the performance of probes as a function of persistence, corresponding to hybridization time-points measured at 1 hour and 24 hours. As in FIG. 17a, the points on both axes are smoothed over 5% of the probes for each point to more effectively show the trends. This metric though reasonably effective at finding some good probes (near the high end of the persistence distribution), is not very efficient at identifying relatively poor probes.

FIG. 17c shows the performance of probes as a function of their HomLogS2B homology scores. Again, the points on both axes are smoothed over 5% of the probes for each point in the plot. As the large majority of the probes have a HomLogS2B>18, most of the probes are within the rightmost region of the plot. Only the bottom 6% of the probes have a HomS2B score <5 and these probes demonstrate particularly low signal slopes and hence poor probe performance. Consequently, this metric is particularly effective in eliminating the relatively small number of probes with low HomLogS2B and poor specificity.

In conclusion, these experiments identified the calculated duplex $T_m$ score and the homology scores as the most effective in silico predictors of good probe performance, and the signal intensity as the best empirical predictor that can be measured in simple experiments that can be performed with small numbers of normal samples, such as self-self experiments.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A computer-implemented method for generating a set of probe nucleic acid sequences, the method comprising:
    (a) sorting a plurality of candidate probe nucleic acid sequences, for a genomic region of interest, from smallest genomic distance to largest genomic distance between neighboring candidate probe nucleic acid sequences to produce a sorted plurality of candidate probe nucleic acid sequences;
    (b) evaluating a probe parameter for a neighboring pair of candidate probe nucleic acid sequences from said sorted plurality to identify a first member of said neighboring pair with a more desirable probe parameter than a second pair member of said neighboring pair;
    (c) removing said second pair member from said plurality;
    (d) reiterating said sorting, evaluating and removing steps at least once to generate a set of probe nucleic acid sequences; and
    (e) outputting said set of probe nucleic acid sequences
    wherein said method is performed by a computer that is programmed to perform said method.

2. The method according to claim 1, wherein said neighboring pair evaluated in step (b) is a pair that is closest to each other in terms of genomic distance in said sorted plurality.

3. The method according to claim 2, wherein said probe parameter is an in silico probe parameter.

4. The method of claim 3, wherein said in silico probe parameter is selected from a group consisting of duplex melting temperature, hairpin stability, GC content, probe is within an exon, probe is within a gene, probe is within an intron, probe is within a intergenic region, and homology score.

5. The method according to claim 1, comprising synthesizing at least one probe nucleic acid having a sequence of a member probe nucleic acid sequence of said set of probe nucleic acid sequences.

6. The method according to claim 5, wherein said method further comprises assaying said probe nucleic acid in a hybridization assay.

7. The method according to claim 1, comprising generating a nucleic acid array comprising at least one probe nucleic acid having a sequence of a member probe nucleic acid sequence of said set of probe nucleic acid sequences.

8. The method according to claim 7, wherein said method further comprises contacting said nucleic acid array with a genomic sample.

9. The method according to claim 4, wherein said evaluating comprises evaluating duplex melting temperature and wherein said first member has a lower duplex melting temperature than said second pair member.

10. The method according to claim 4, wherein said evaluating comprises evaluating homology score and wherein said first member has a higher homology score than said second pair member.

11. The method according to claim 1, wherein said plurality of candidate probe nucleic acid sequences are generated by:
    (i) selecting target sequences from said genomic region of interest;
    (ii) repeat-masking said target sequences to form non-repeat masked regions;
    (iii) tiling sequences across said non-repeat masked regions to generate said candidate nucleic acid sequences; and
    (iv) screening said candidate probes nucleic acid sequences according to at least one in silico parameter.

12. The method according to claim 11, comprising identifying restriction enzyme sites in the genomic region of interest, and selecting target sequences that exclude said restriction enzyme sites.

13. A non-transitory computer readable medium comprising instructions for performing the following method:
   (a) sorting a plurality of candidate probe nucleic acid sequences, for a genomic region of interest, from smallest genomic distance to largest genomic distance between neighboring candidate probe nucleic acid sequences to produce a sorted plurality of candidate probe nucleic acid sequences;
   (b) evaluating a probe parameter for a neighboring pair of candidate probe nucleic acid sequences from said sorted plurality to identify a first member of said neighboring pair with a more desirable probe parameter than a second pair member of said neighboring pair;
   (c) removing said second pair member from said plurality;
   (d) reiterating said sorting, evaluating and removing steps at least once to generate a set of probe nucleic acid sequences; and
   (e) outputting said set of probe nucleic acid sequences.

14. The non-transitory computer readable medium of claim 13, wherein said neighboring pair evaluated in step (b) is a pair that is closest to each other in terms of genomic distance in said sorted plurality.

15. The non-transitory computer readable medium of claim 14, wherein said probe parameter is an in silico probe parameter.

16. The non-transitory computer readable medium of claim 15, wherein said in silico probe parameter is selected from a group consisting of duplex melting temperature, hairpin stability, GC content, probe is within an exon, probe is within a gene, probe is within an intron, probe is within a intergenic region, and homology score.

17. The non-transitory computer readable medium of claim 16, wherein said evaluating comprises evaluating duplex melting temperature and wherein said first member has a lower duplex melting temperature than said second pair member.

18. The non-transitory computer readable medium of claim 16, wherein said evaluating comprises evaluating homology score and wherein said first member has a higher homology score than said second pair member.

19. The non-transitory computer readable medium of claim 13, where said plurality of candidate probe nucleic acid sequences are generated by:
   (i) selecting target sequences from said genomic region of interest;
   (ii) repeat-masking said target sequences to form non-repeat masked regions;
   (iii) tiling sequences across said non-repeat masked regions to generate said candidate nucleic acid sequences; and
   (iv) screening said candidate probes nucleic acid sequences according to at least one in silico parameter.

20. The non-transitory computer readable medium of claim 19, wherein said method comprises identifying restriction enzyme sites in the genomic region of interest, and selecting target sequences that exclude said restriction enzyme sites.

* * * * *